(12) United States Patent
Young

(10) Patent No.: US 6,179,786 B1
(45) Date of Patent: Jan. 30, 2001

(54) SYSTEM FOR THERMOMETRY-BASED BREAST CANCER RISK-ASSESSMENT

(75) Inventor: David E. Young, Watlington (GB)

(73) Assignee: Profemme Ltd., Witney (GB)

( * ) Notice: Under 35 U.S.C. 154(b), the term of this patent shall be extended for 0 days.

(21) Appl. No.: 09/385,387

(22) Filed: Aug. 30, 1999

Related U.S. Application Data

(60) Provisional application No. 60/102,882, filed on Oct. 2, 1998.

(51) Int. Cl.$^7$ ................................. A61B 5/00; A61B 5/04
(52) U.S. Cl. .................... 600/549; 600/388; 600/386; 600/382; 600/372
(58) Field of Search .................... 600/549, 388, 600/386, 389, 390, 393, 382, 372, 306, 300, 551

(56) References Cited

U.S. PATENT DOCUMENTS

| | | | | |
|---|---|---|---|---|
| Re. 32,000 | * | 10/1985 | Sagi ........................... | 600/549 |
| 3,830,224 | * | 8/1974 | Vanzetti et al. ............. | 600/549 |
| 3,847,139 | * | 11/1974 | Flam .......................... | 600/549 |
| 3,960,138 | | 6/1976 | Doss et al. . | |
| 4,190,058 | * | 2/1980 | Sagi ........................... | 600/549 |
| 4,524,778 | * | 6/1985 | Brown, Jr. et al. .......... | 600/549 |
| 4,624,264 | * | 11/1986 | Sagi ........................... | 600/549 |
| 4,651,749 | * | 3/1987 | Sagi ........................... | 600/549 |
| 5,301,681 | | 4/1994 | DeBan et al. . | |
| 5,813,404 | * | 9/1998 | Devlin et al. ............... | 600/372 |
| 5,830,159 | | 11/1998 | Netta . | |
| 5,941,832 | * | 8/1999 | Tumey et al. ............... | 600/549 |
| 5,999,843 | * | 12/1999 | Anbar ......................... | 600/549 |
| 6,077,228 | * | 6/2000 | Schonberger ............... | 600/549 |
| 6,086,247 | * | 7/2000 | von Hollen ................. | 600/549 |

FOREIGN PATENT DOCUMENTS

PCT/US90/ 02203   11/1990   (EP) .

2 203 250   10/1988   (GB) .

OTHER PUBLICATIONS

Simpson, Griffiths et al., "The lutoal heat cycle of the breast in health", 27 Breast Cancer Research and Treatment, 239–45 (1993).

Sir James Young Simpson, Memorial lecture 1995 "Breast Cancer Prevention (a pathologist's approach)", J.R. Coll, Surg. Edinb., 41 (Jun. 1996).

Simpson, et al., "The lutoal heat cycle of the breast in disease", Breast Cancer Research and Treatment (1995).

Simpson, et al., "A clinical test for breast pre–cancer". A Journal of Chronobiological Research in Medicine, The. 1, N.1 (1995).

* cited by examiner

Primary Examiner—Cary O'Connor
Assistant Examiner—Navin Natnithithadha
(74) Attorney, Agent, or Firm—Tilton, Fallon, Lungmus & Chestnut

(57) ABSTRACT

The system provides analogue electronic sensor means, novel mechanical harness mounting means having adjustment means and provided with remote attached monitor control means for sampling breast surface temperature and means for collecting, storing and displaying these data. The system allows breast temperatures to be measured, with great reliability, for periods of an hour or more at any desired rational sampling rate. Collected breast surface temperature data may then be downloaded into a computer for elaboration using proprietary software. Breast surface temperatures are measured at a specific point during the menstrual cycle, determined by progesterone levels in the urine. The data obtained with the instant invention under these conditions enables an investigator to determine, in women who have not reached the menopause, those who are at risk of developing breast cancer at some time in the future and those who are not at significant risk of developing the disease.

58 Claims, 11 Drawing Sheets

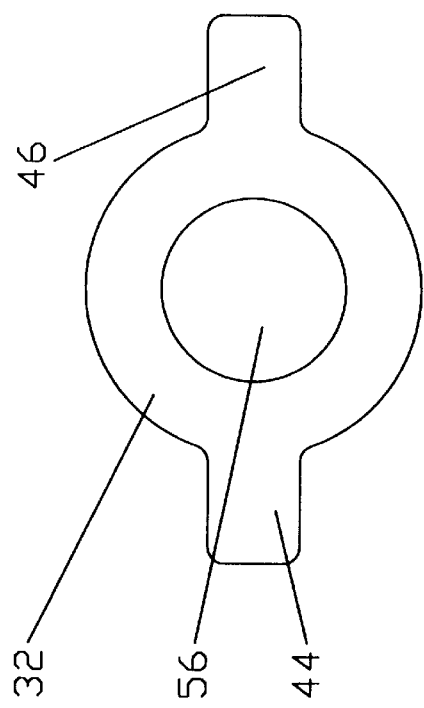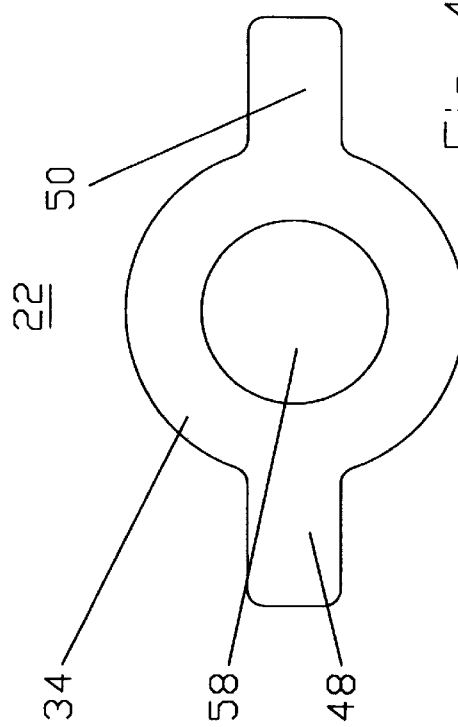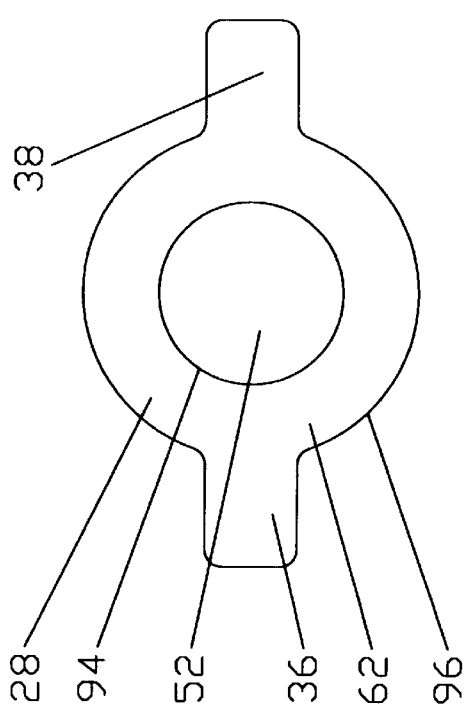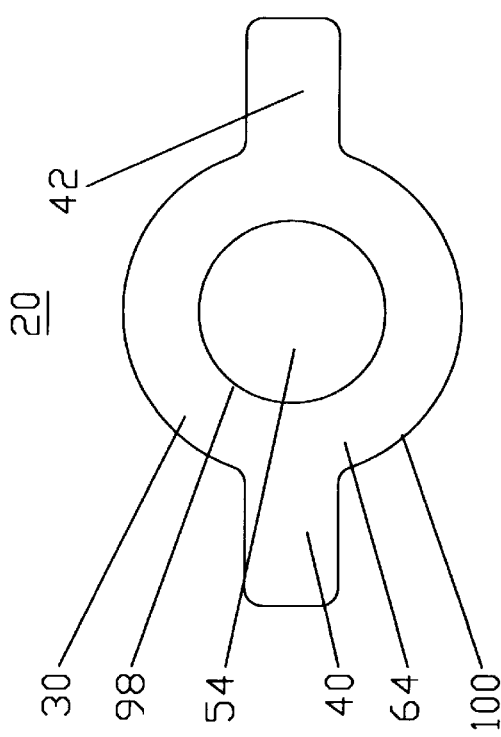
Fig 4

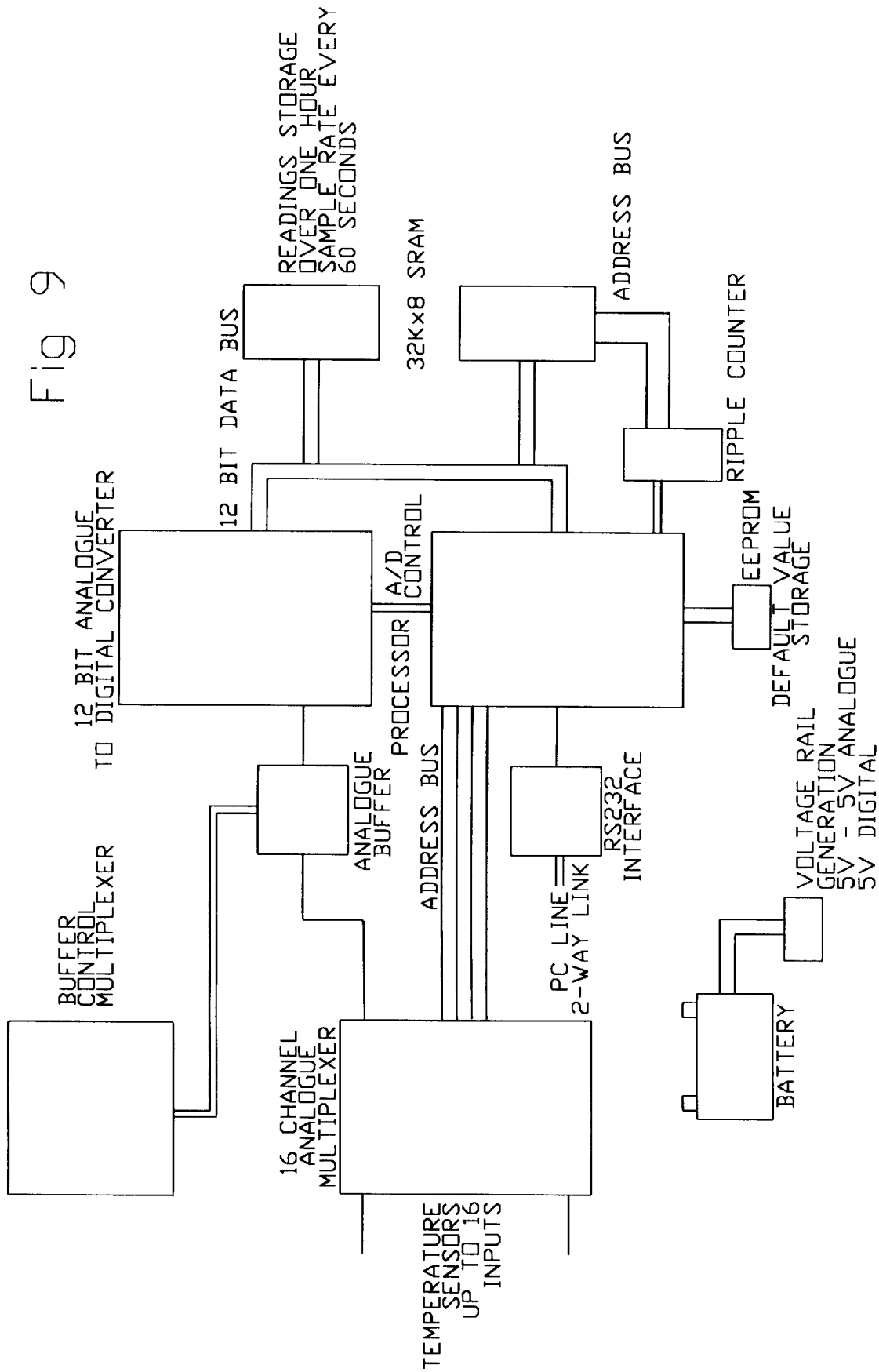

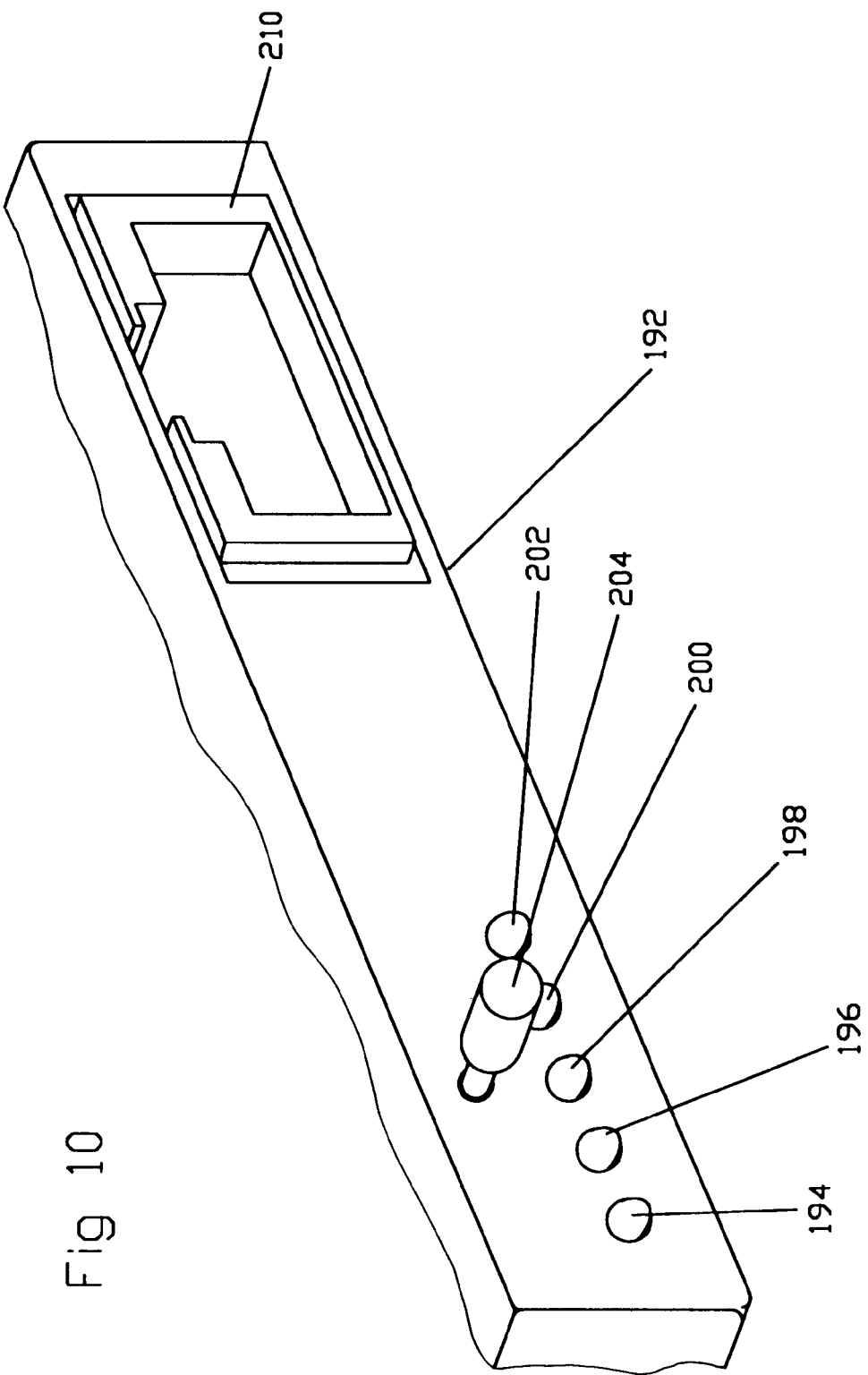

SYSTEM FOR THERMOMETRY-BASED BREAST CANCER RISK-ASSESSMENT

REFERENCE TO RELATED APPLICATIONS

This application is entitled to the benefit of the filing date of Provisional Application No. 60/102,882, filed Oct. 2, 1998 with respect to all subject matter common to both applications.

FIELD OF THE INVENTION

The present invention is in the field of biotechnology and specifically relates to the field of breast cancer screening in women.

BACKGROUND TO THE PRESENT INVENTION—THE RELATED ART

For well over twenty years, thermometric assessment of the human female breast surface has been under investigation as a tool in the armamentarium of those concerned with the detection and treatment of breast cancer.

GB 1,492,803 (expired) and U.S. Pat. No. 4,055,166 (expired), both granted to Simpson and Green and of substantially identical content, describe a garment which is a brassiere upon and within which is mounted a plurality of sensors for the purpose of measuring breast temperature over the menstrual cycle. They referred to a menstrual cycle of breast heat amounting to a variation in surface temperature of about 1° C. which is maximal about 3 days before the onset of menstruation. In the preamble, it is made clear that the intention is to detect the presence of actual cancers based on the observation that areas adjacent to a cancerous growth may be "slightly warmer (say 1 or 2° F.) than unaffected areas of the other breast" and that comparison of the 24 hour temperature variation (circadian variation) between normal and cancerous breasts have shown clear differences in time structure.

These authors make an important structural distinction between their brassiere device and the earlier breast surface measurements which had been made in hospital environments with sensors fixed on the skin. They taught the provision of a garment which would allow temperature measurements to be recorded over relatively long periods while the subject lives normally. They provide "apparatus for measuring surface temperatures at points in the region of the human body, including a garment having a plurality of temperature sensors located therein at spaced apart positions, and means for so storing signals representing output signals from the sensors that the relationship of each signal time of occurrence can be retrieved".

In particular, they indicate a preference for the storage means to be mounted on the garment. According to Claim 1 of U.S. Pat. No. 4,055,166, the garment and the means for storing signals are integral,. In Claim 1 of GB 1,492,803 the apparatus includes a garment and Claim 4 and various other dependent Claims describe a brassiere which includes sampling and storage means being integral with the brassiere.

Simpson and Green make it clear that, in relation to measurements of temperature on the breasts, the garment may be a brassiere. They teach a brassiere for measuring surface temperatures of the breasts at predetermined points, including a plurality of temperature sensors positioned in each cup of the brassiere the sampling and storage means being integral with the brassiere.

Their underlying contention is that "The circadian rhythm of breast temperature is regarded as normal feature of the mammary tissue differentiation—a response possibly of a target organ to tides of hormones in the circulation (e.g., 24-h variations in prolactin; menstrual variations in oestrogen). Consequently alterations of the circadian rhythm characteristics occur in breast pathology of which cancer is one example. In this situation the rhythm is sometimes absent and often of altered level and phase. It follows that monitoring breast temperature rhythm over daily and perhaps monthly intervals will be valuable in detection and characterization of disease, e.g., cancer." From this and other statements in the specification it is clear that these authors did not contemplate the application of their invention in the assessment of the future risk of developing cancer and that it was limited to detection of and characterizations of actual lesions.

The Simpson and Green patents teach a brassiere fitted with temperature sensors positioned at points where tumors have been shown to occur most frequently—at one, two and three o'clock, over the nipple and at nine o'clock on the left breast, and on the right breast there is a similar concentration of sensors over the upper outer quadrant, that is at nine, ten and eleven o'clock with a sensor over the nipple and one at three o'clock. They do contemplate different positioning of the sensors and that a different number may be deployed.

What is quite clear, however, is that their device as described, is a garment fitted with temperature sensors and having means for storing signals from the sensors included with or integral with the garment. It is also quite clear from the detailed descriptions and claims that when the apparatus is to be used on the human breast, the garment is to be a brassiere. They also clearly describe, in Claim 6 of each patent, the use of a heat shield to prevent outward heat flow through the sensor.

Simpson has since suggested that the device, which is the subject of the test described in the two patents, is subject to 'noise' and that this is due to other vasomotor phenomena. He has suggested that "The problem with the method is not the signal, but the noise from these sources." *Sir James Young Simpson Memorial Lecture, J. R. Coll. Surg. Edinb.,* 41, June 1996. He goes on to suggest that future developments could include Doppler ultrasonography applied to the internal mammary artery and volumetric analysis of the breast and its component tissue using magnetic resonance imaging.

In the source quoted above, Simpson makes it clear that his developments are nowadays directed at trying to predict, from temperature measurements, which breasts may develop cancer later.

Although Simpson and Green appear to have been the first workers to make a serious attempts at detecting breast cancer by observing breast surface temperatures, theirs is not the only work. Detectors for actual cancer lesions based on breast surface temperature are still being developed and this is somewhat surprising since most authorities believe that tumors large enough to find by this method are already likely to be have progressed so far as to carry with them fatal consequences.

One example is BreastAssure™ made in the U.S.A. by HumaScan Inc of Cranford, N.J. The makers claim that this device is the subject of two U.S. patents which expired on May 22, 1998 and a Canadian patent expiring on Aug. 24, 1999; these are all believed to be to Z. L. Sagi. Financial literature on the company states the product "consists of a pair of mirror-image, non-invasive, lightweight, disposable soft pads, each of which has three wafer-thin segments containing columns of heat sensitive chemical sensor dots that change color from blue to pink reflecting an 8.5° temperature range from 90° to 98.5° F. When placed over a woman's breasts, inside her brassiere for a period of 15 minutes, the device registers skin temperature variations due to heat conducted from within the breast tissue to the surface of the skin. By comparing the mirror-image temperature differences between the two breasts registered by the device, the physician can objectively quantify if there is abnormal unilateral breast thermal activity, which is considered significant if there is a 2° F. or more temperature difference between each breast in the same mirror-image location. Based on clinical studies at major medical centers, the threshold tumor size that resulted in significant skin temperature differences detectable with the device was as small as 5 mm in size." It may be worth noting that, according to some authorities, cancers of this size may well have already metastasized. Other experts to whom I have spoken doubt whether 15 minutes is an adequate time for any device placed on or over the breasts to equilibrate with breast temperature on a consistently reliable basis.

The manufacturer claims that according to industry sources, the majority of breast tumors are, on average, at least 15 mm or larger before they are palpable by most experienced clinicians. Literature which I have seen suggests that 15–20 mm is the range in which most become tumors become palpable.

Another recent entrant to this field is Biofield Inc of Roswell, Ga., U.S.A., with its ALEXA™1000 system. According to material released by the company onto the Internet, this employs single-use sensors and a measurement device to analyze changes in cellular electrical charge distributions associated with the development of epithelial cancers such as breast cancer. Sensors are arranged on the skin surface in and around the quadrant of the breast where a suspicious lesion has been identified and in corresponding locations on the asymptomatic breast. Sensor readings are measured and analyzed using a pre-programmed algorithm. The technology is claimed to be based on the observation that epithelial cancers are characterized by uncontrolled recurrent cell proliferation of rapid cell division. As these cells divide, an electrical charge is released. This results in a disruption, or depolarization, of the charge distribution found in normal epithelial tissue. Moreover, the depolarization appears to be progressive as cell transformation and carcinogenesis occur. It is claimed that this depolarization is measurable at the skin surface in the form of electrophysiological differentials. The final output is a single numerical and objective value, from 1 to 30. The result of this test is claimed to provide an indication of the proliferation level, which is related to the probability as to whether a lesion is malignant or benign. The manufacturer claims that a task force sponsored by the European School of Oncology has reported on the measurement of electropotentials from the breast as a possible method of detecting breast cancer. This report summarizes the background and early results and suggest that this technique may have a role in the diagnosis of both palpable and non-palpable breast lesions. U.S. Pat. Nos. 5,427,098; 5,560,357; 5,415,164; 5,217,014; 5,320,101 and 5,099,844 all appear to relate to this technology. I have been unable to verify these claims from enquiries made with the European Institute of Oncology, which is a current trial center for the instant invention.

Lifeline BioTechnologies Inc, another U.S. company, has two products which are claimed to increase the chance of finding potential breast cancers at an early stage. The KELLY MONITOR is a detection aid for early breast cancer apparently intended for use as a non-invasive complement to mammography. It consists of sensors and a small portable data storage unit, worn for up to forty-eight hours in order to capture temperature patterns which are stored for later analysis. The device dynamically monitors the physiologic activity of the breast by means of circadian rhythm analysis. This monitor uses a sixteen sensor array: seven for each breast, one for the sternum, and one to measure ambient temperature and, like the Simpson and Green disclosure, calls for placement determined by occurrence data for breast cancer. This product uses a proprietary template for identical placement on each breast. The manufacturer's literature claims to use sensors which are considered "interchangeable", eliminating the need for insulation, adjustable resistors, and continued calibration. This commercial claim appears to be directed in a negative manner at the Chronobra™, a device based on Simpson and Green's patents which does require the use of calibration and trimming resistors. It is not clear whether this product is the subject of either an issued patent or a patent application.

Unlike the other devices and products hereinbefore described, the FIRST WARNING™ product is claimed to identify women who will eventually develop breast cancer and to be a 'Risk-Marker'. The literature indicates that during the test, a custom-designed breast temperature sensor is integrated into a cup insert for use with the patient's brassiere, and she will be directed to place the sensors directly within her brassiere and thus on her breast. The patient would be required to wear the device for ninety minutes each night. The sensor is intended to measure surface temperature over the breast area for each breast throughout this period. The inserts are apparently presented in several sizes to fit the wide variation in breast sizes in the female population. According to the literature, each sensor will detect the unique temperature patterns of the breast. The sensors are described as connected to a miniature storage device which is worn concealed under the clothing. The literature indicates that at the conclusion of the test, the device is plugged into a data storage unit which is small enough to be placed on a bedside table. The data is transferred to the base and the portable unit is recharged. An additional requirement described is for a sample of saliva to be taken on a daily basis. The saliva is placed in a small vial and stored in a refrigerator in a special calendar/date related container until the test concludes. The entire test lasts for thirty days. The results are then analyzed using proprietary techniques to assess the risk factor for the patient. The company claims that traditional statistical techniques are not accurate enough in their discrimination of the data. The ultimate result is an indication of high or low risk. The product is believed to the subject of a U.S. patent application.

The practicality of this test seems to be questionable at least. It has to be done over thirty days and thus requires an enormous level of compliance in today's fast-moving world where many women do not have well ordered lives which allow them to be constantly at home. This test also has to be done for ninety minutes each night, followed by a procedure to re-charge the monitor; it is surely rather likely that the patient would fall asleep. The most limiting factor, however, is likely to be the sheer cost of 30 hormonal assays for each patient. On top of this is the question of available laboratory capacity to carry out the tests—on the basis of the manufacturer's own figures, they hope to generate a level of business per 'developing family practice' which would produce a laboratory load of 3,100 hormone assays.

With the exception of the last product described, all prior art items which I have been able to find may be called breast cancer detection aids. As such, their use is limited, since any patient who already has cancer has a reduced risk of survival and a certainty of morbidity. On the other hand, any patient who tests negative, is only negative on the day of the test and has no idea of her future risk status.

Since most authorities now accept that about 1 in 12 women in Europe and maybe as many as 1 in 10 in the U.S.A., dies from breast cancer and up to 1 in 8 may develop the disease at some point in their lives, it would clearly be of enormous benefit to be able to identify which women are at risk and which not. By such a means of risk-assessment, very great relief from stress could be imparted to the majority of women. Even women found to be at risk would be much better off since the health care system, whether public or private insurance based, would be able to release funds to enhance their surveillance, implement better avoidance strategies (perhaps involving diet and nutritional supplementation) and treat them better, should the disease eventually supervene. I estimate that in the UK alone, having an effective means for positively identifying those who are at risk and three quarters of those who are not at risk, would save £1.8 billion per annum, as well as avoiding a vast amount of human misery.

Clearly, there is room for substantial improvement in the management of breast cancer since the long term survival prospects, following diagnosis, are still not very encouraging, barely exceeding 50%. Mass campaigns directed at self-examination are not very successful since, even when regularly practised, women who find lumps which turn out to be malignant upon biopsy generally detect these at a size which is lethal. This is particularly so in young women with dense breast tissue.

It may be that today's limited success in treating this disease is partly due to the failure to recognise pre-cancerous states in mammary tissue as a whole. The investigation, observation and tracking of these states would allow earlier diagnosis and would also permit potential intervention strategies to be exploited perhaps with marked effects on ultimate survival rates.

Work published by Simpson and others, well after the date of his patents, includes comparative microscopy data in cancer-associated breasts and age-matched normal breasts showing a gross excess of focal hyperplasias in pre-menopausal cancer-associated breast tissue. Additionally, epidemiological data are consistent with this finding in that such tissue is subject to a 6-fold increased risk of further primary carcinogenesis. In addition, it is now known that premenopausal mammary tissue goes into a monthly pregnancy rehearsal with glandular proliferation and increased blood supply. These phenomena have been shown to produce a luteal heat cycle which produces a variation in breast surface temperature of about 1° C. in normal women (probably not at risk of cancer). Women with cancer-associated breasts exhibit only up to about half this amplitude. The pattern of temperature rise is also different insofar as the temperature rise curve in cancer-associated breasts is relatively steady and peaks earlier in the menstrual cycle than in normals. Normals exhibit a high correlation with and dependence upon endogenous progesterone levels during the luteal phase.

The differences in breast temperatures between 'normal' women and clinically normal women with cancer-associated breasts, measured during the luteal heat cycle, are maximal during the few days just after ovulation. Breast temperature variations may be associated, at least in part, with abnormal breast arterial blood flows at particular phases of the menstrual cycle. Significantly increased blood flow commences at the start of the luteal phase, some fourteen days prior to menses. The blood supply of the breast is from the axillary artery via the lateral thoracic and acromio-thoracic branches and also from the internal mammary (thoracic) artery via its perforating branches. In the female, the branches of the second, third and fourth intercostal spaces give branches to the breast which vary in size under hormonal bombardment. Thus although the contribution to overall elevation in breast temperature may be greater by some arteries than others, all exhibit a menstrual cycle of breast blood flow and all contribute to the breast luteal heat cycle.

In any system or device for breast surface temperature measurement which is to have broad applicability for mass screening of populations, great attention has to be given to practicability. Any such entity which consumes large amounts of time in setting up will be unacceptable.

For this reason, the physical attachment of sensors to the breast surface of subjects has not proven popular. The need to apply each sensor separately, usually with adhesive tape, is not only time consuming but has obvious disadvantages for the subject at the time of removal. There is also the problem of ensuring that individual sensors do not become detached as a result of traction on cable connecting means employed to deliver the signal to whatever means is employed for temperature data collection.

The use of a sensor array, integral with a brassiere, this garment also having means for carrying a data logging device, is apparently, the preferred implementation of the Simpson and Green utilities. This device has the name Chronobra™ and Simpson has published on this in the lay press as recently as September 1997. It is clear from other publications on this device that, although it has some functionality, there are inherent problems of poor signal, intermittent signal and sometimes a complete absence of signal, logged from certain individual sensors suggesting poor and inconsistent contact between these and the breast surface.

Analysis of the device, an example of which I have obtained, suggests that the problems are unlikely to be truly electrical but are related to the structure and mechanics of the device. The manner in which thermal sensors and the garment are integrated involves the use of a sewn-in lining pad made of stiff material and provided with a plurality of perforations. A plurality of thermal sensors is each encapsulated within in a thick moulding of silicone material which is in the shape of a cylindrical plug which is 'T' shaped in cross-section, each sensor being located in the 'leg' of a 'T'. The sensor mouldings are disposed between the perforated lining pads and the cups of the brassiere. Each perforation in the lining pad accommodates the leg portion of one thermal sensor moulding so as to present it to the breast surface.

I have measured the thickness of the silicone mould material disposed about a number of sensors and in no case was this less than 2.0 mm. However, the least thickness measured at the end of a moulding over that surface of the sensor directed towards the breast was 3.1 mm and in some cases over 4.0 mm. Since silicone rubbers are highly effective insulating materials with poor thermal conductivity it is certain that this arrangement will lead to reduced effectiveness and possibly to repeated low readings. Simpson and Green's disclosures call for insulating means to prevent heat loss and this may be why they employed a large plug of the selected material behind the sensors. However, to employ such a material over the face of the active thermal sensing element suggests a fundamental misunderstanding of the principal aim at hand. This is the measurement of small variations in temperature of a target in an ambient environment, the temperature of which is not vastly different from the target itself. Under these circumstances, the principal aim is only likely to be met either when there is no barrier at all or, if there is one, it has high thermal conductivity and minimal thickness.

Further analysis of the subject Chronobra™ device, both on and off subjects, suggests other reasons why instances of intermittent or absent signal are encountered. First, the integral construction of the sensor array and brassiere called for by the Simpson and Green patents and embodied in the use of a lining pad, leads to a rather rigid cup construction which resembles a rounded modified cone. In most women, the breast surface is profoundly convex on the lower aspect and somewhat concave on the superior aspect. Such a mis-match of profiles explains why, in a number of cases, the sensor mouldings of the upper aspect of the cups do not come into contact with the superior breast surface at all. Such a brassiere must, of course, be available in all rational sizes if a general population is to be tested. This inevitably increases the cost and level of inconvenience associated with the test. Mounting the data logging device on the brassiere—which reads for the Simpson and Green patents—between and below the cups, introduces traction on the brassiere and exacerbates the non-contact problem by pulling the upper surfaces of the cups away from the breast surfaces. Each fine, twisted pair of sensor connecting leads extends from the sensor to the data logging device separately and without further protection. This not only makes for an untidy appearance but also increases the risk of tangling and traction on individual sensors. Finally, this device does not use any form of true calibration and therefore it cannot be argued that the output from the sensors represents accurately any particular absolute temperature.

OUTLINE OF THE PRESENT INVENTION

This invention is based on the observation that, in general, pre-cancerous states of the breast as well as cancer may be recognised by observing beast temperature.

As noted, prior art devices are in the form of sensors physically attached to the breast surface, brassieres with integral sensors or brassiere inserts which fit within and which are retained by the cups of a brassiere. Furthermore, with only one exception, all of those which I have been able to find are concerned with the detection of an actual cancerous lesion.

In marked contradistinction to prior art devices, the instant invention is neither physically attached to the breast surface and is also neither a brassiere nor a brassiere insert. Furthermore, it is directed, by means of the function of its structural elements, towards the assessment and determination of the risk of developing cancer later in life, by the measurement of breast temperatures, over a period normally of one hour. Notwithstanding this, the instant invention may be used to detect breast cancer.

In the system of the instant invention, a universal harness, only one size of which is needed to fit all subjects, comprises two flexible, flat, ring-like contactor pads, united anteriorly by a short, adjustable, elasticated strap and united posteriorly by a longer, adjustable and openable strap. The harness may be used in conjunction with the patient's own brassiere or without a brassiere, according mainly to the choice of the investigator. Each contactor pad comprises substantially similarly sized and shaped inner and outer layers of flexible, compressible and extensible material which, conveniently, may be neoprene, provided with suitable flexible facing fabrics, such as the nylon material known commercially as Lycra™.

Each contactor pad layer has two extension tabs, disposed about opposite ends of a diameter, for the attachment of the short anterior strap and the longer, openable, posterior strap. The contactor pad layers each have a central hole which is so sized that it will accommodate the areolar area of the majority of women and is conveniently about 50 mm in diameter. The outer diameter is conveniently about 100 mm. The inner and outer contactor pad layers are laid one over the other such that the extension tabs are aligned and are then stitched together around the circumference of the central hole.

An array of thermal sensors, preferably but not necessarily four in number, is disposed about the inner surface of the inner contact pad layer in a regular manner along the circular center line lying between the inner and outer boundaries. The sensors are preferably of the analogue type which produce a current in proportion to temperature and are housed in a transistor can package. Each sensor of this type has three wire legs which are introduced through the material of the inner contactor pad layer. The neoprene material effectively self-seals against each sensor leg. The sensor cans are completely unsheathed, having no additional covering of any kind in order to ensure contact with the breast surface and to maximise thermal transfer.

The three legs of each can package each engages a small disc-like moulding, provided with through holes disposed, in its periphery, 120° apart. The legs are then be bent over at the periphery of the disc providing initial securing means for this assembly. Cable connecting means are in the form of light, flexible plastics sheathed outers each provided with a plurality of twisted pairs of inner cables, the number of pairs being the same as the number of sensors provided on each contactor pad. It is strongly preferred that a different color outer cable covering is used for each contactor ring and that a convention is adopted, during use, that the first color is always used with a first breast and that the second color is always used with a second breast. Wiring is accomplished according to a novel strategy directed to towards ensuring that individual sensors are never subjected to traction in normal robust use.

Flexible insulating and cushioning means are introduced intimately about the sensor legs and connections and between the contactor pad layers which are then sewn together to complete the contactor pads. These are soft and compressible and have a 'bulked' feel. The contactor pads are 'handed' and the sheathed outer of the cables are directed medially. A short, elastic, adjustable anterior strap is sewn between medial tabs on each contactor pad. A longer elasticated, adjustable and openable posterior strap, is sewn to laterally directed tabs on each contactor pad.

The colored connecting cables terminate within the case of a monitor unit and preferably have a softness such that they drape readily under their own weight. This monitor is provided with electronic micro-circuitry which provides timing and memory means capable of polling each sensor, every sixty seconds, for one hour and storing the data so collected. The sensors are preferably independently calibrated to within 0.01° C. using pre-set potentiometer means located within the monitor unit. The monitor is preferably powered by a re-chargeable nickel hydride battery. The monitor is provided with a series of colored LEDs which indicate status of the system under a variety of conditions.

The temperature sensing cycle is initiated by depressing a plunger and the monitor unit switches off automatically at the end of the sensing cycle.

Data stored within the monitor is downloaded to a host PC via an interface unit to which it is attached with suitable connecting cable and plug means. The interface also provides charging means and this function is activated upon connection, whether the monitor is downloading or not. Conveniently, the interface will provide charging services for a plurality of monitor units, typically twelve at one time. The host PC, which preferably has a 100 MHz processor or better and uses the Windows 95™ operating system, is provided with a dedicated programme written, for instance, in Turbo-Pascal™ for Windows™. This programme is capable, under keyboard or mouse command, of communicating with the monitor unit, initiating data download, capturing and saving downloaded data and displaying this in graphical and tabular form for each sensor. In addition the programme provides means for pictorial graphic display of the temperature measured by each sensor, at each polling, displayed in its correct spatial position on each breast.

Re-setting the monitor unit for further use is normally carried out from within the host computer, using software means, however, should there be a reason to abort a sensing cycle and start another, this is accomplished by depressing a re-start button mounted sub-flush with respect to the surface of the monitor case.

In use, the subject to be investigated, who will generally be between 20 and 50 years of age and in any event will not have reached the menopause, is counselled upon recruitment as to the nature of the test. Some time prior to the test, she is provided with a urine dip test kit which will indicate the day upon which she has a marked rise in luteinising hormone. She is also provided with a series of sterile bottles in which to collect a series of at least three early morning saliva samples which, when the series is complete are forwarded, in the container provided, to a suitable laboratory equipped to carry out assays of progesterone levels. These results are used to measure and predict the most suitable date in the subject's next cycle to carry out the breast temperature test.

On the appropriate day, the subject is called to the location where the test is to be conducted. In a warm environment, where the ambient temperature should be 24° C.±2° C., the subject is fitted with the harness of the instant invention. The patient may, in addition, wear her own brassiere if she wishes, or a sports type elasticated brassiere or no brassiere. She should, however, wear a substantial and close fitting over garment, to limit or prevent any generalised heat loss. It is essential that identification details relating to both the subject and the monitor unit are recorded together and that the integrity of this combined information is maintained. Only one size of the instant harness is normally provided and required.

The sheathed connecting leads between the harness and the monitor unit are led out from under the lower margin of the over garment. To start the test, the assistant, helper or other designated person depresses the plunger on the monitor unit, observing that the 'start' LED illuminates, to confirm initiation of the test. It will be found convenient if the subject is provided with a dressing gown in order that the monitor unit may be placed in a pocket during the test. Throughout the test period, the subject should be encouraged to sit quietly and avoid exertion and should not imbibe hot or stimulating liquids. At the end of one hour the test will be complete and the patient may return to a private cubicle to doff the harness and dress in her normal clothing prior to departure from the test center.

The data from the monitor unit used with the subject is downloaded into the computer, as hereinbefore described and evaluated by a skilled trained person capable of comparing the subject's breast temperature data with known norms with a view to reaching a conclusion concerning whether or not subject may be at risk of developing breast cancer at a future date.

In the event that this conclusion is positive, the subject would be informed promptly and invited back to participate first in a re-test and then in other tests. The purpose of these is to establish whether or not she may have existing cancer since, although the object of the test of the instant invention is not, primarily, to detect actual cancers, there will be some subjects who come forward who do have the undiagnosed condition. If she is negative to other tests for cancer, she will be informed that she is at a significant risk of developing breast cancer subsequently. This knowledge, allows surveillance, prevention and future intervention strategies to be planned and implemented. These factors, in turn, improve the chances of preventing the disease or should it prevail, successfully treating it at an early stage.

On the other hand, if the test is negative, the subject will also be so informed. In this event, the subject may well be reassured, however, she should be advised that she should return for re-testing at a suitable interval which may be, say, two years. In any case, a follow up record and call-forward system should be maintained in order that any subjects which test negative can be called for a re-test after a suitable period.

The foregoing equipment of the instant invention is undergoing human trials at The European Institute of Oncology, Milan, Italy according to a protocol which reflects the general method of use immediately hereinbefore described. Progesterone assay services are being provided by BioClinical Services Limited, Willowbrook Laboratories, St Mellons, Cardiff, Wales, UK.

Accordingly it is a first object of the present invention to provide a device capable of making accurate measurements of temperatures on the surface of the human breast, particularly the female breast.

It is a second important object of the present invention to reliably record and store measurements of temperatures on the surface of the human breast.

It is a third important object of the present invention to manipulate and display temperature data collected from the surface of the human breast.

It is a fourth important object of the present invention to provide a method for the assessment of the risk of subsequent development of breast cancer in women who do not currently have the disease.

It is yet another object of the present invention to provide a method for the detection of breast cancer in women.

Other features, objects and advantages will become apparent from the specification and drawings in which:

DESCRIPTION OF THE DRAWINGS

FIG. 4, is a plan view of four contactor pad layers, employed in the construction of two contactor pad assemblies, which are deployed in the harness of the present invention.

FIG. 9, is a block diagram of the circuitry employed in the instant system.

FIG. 10, is a diagrammatic representation of the LED display used on the monitor unit of the instant system.

DETAILED DESCRIPTION OF THE INVENTION AND METHOD OF USE

Figure 1:
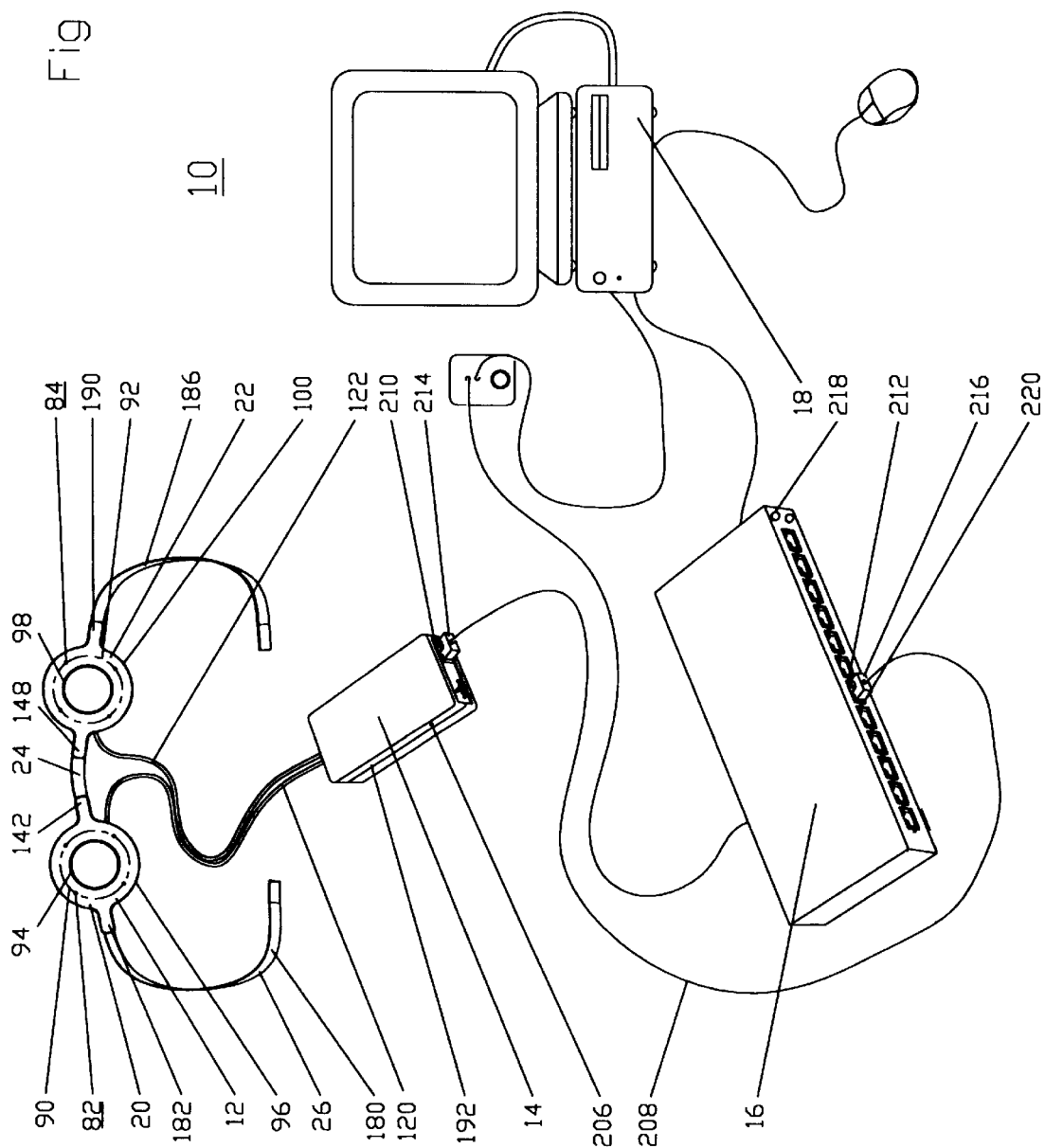
FIG. 1, is a diagrammatic perspective view indicating the principal elements of the system of the instant invention.
Figure 2:
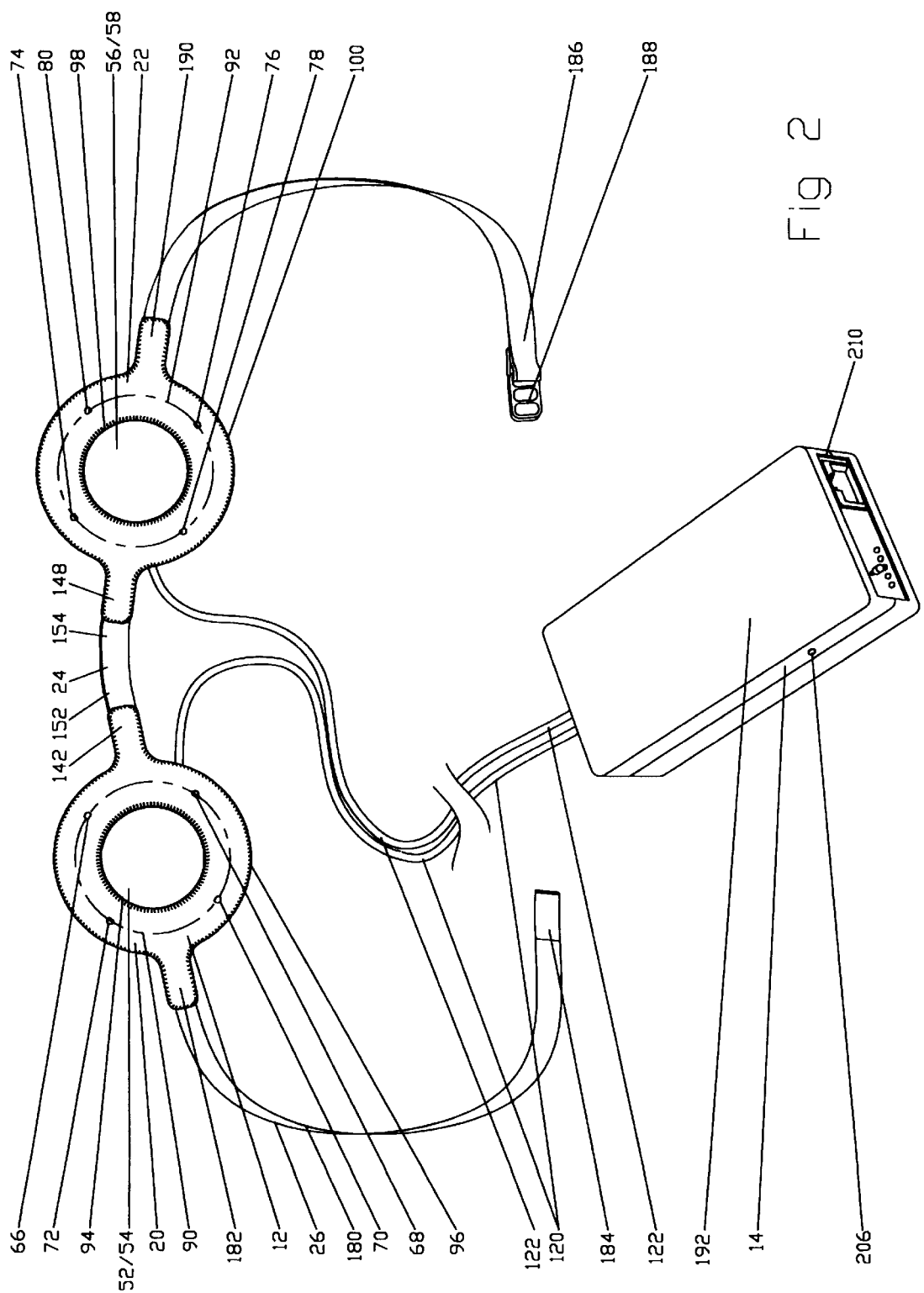
FIG. 2, is a diagrammatic, perspective, view of a most preferred embodiment of a harness and monitor unit according the present invention, showing the inner, functional surface of the harness.
Figure 3:
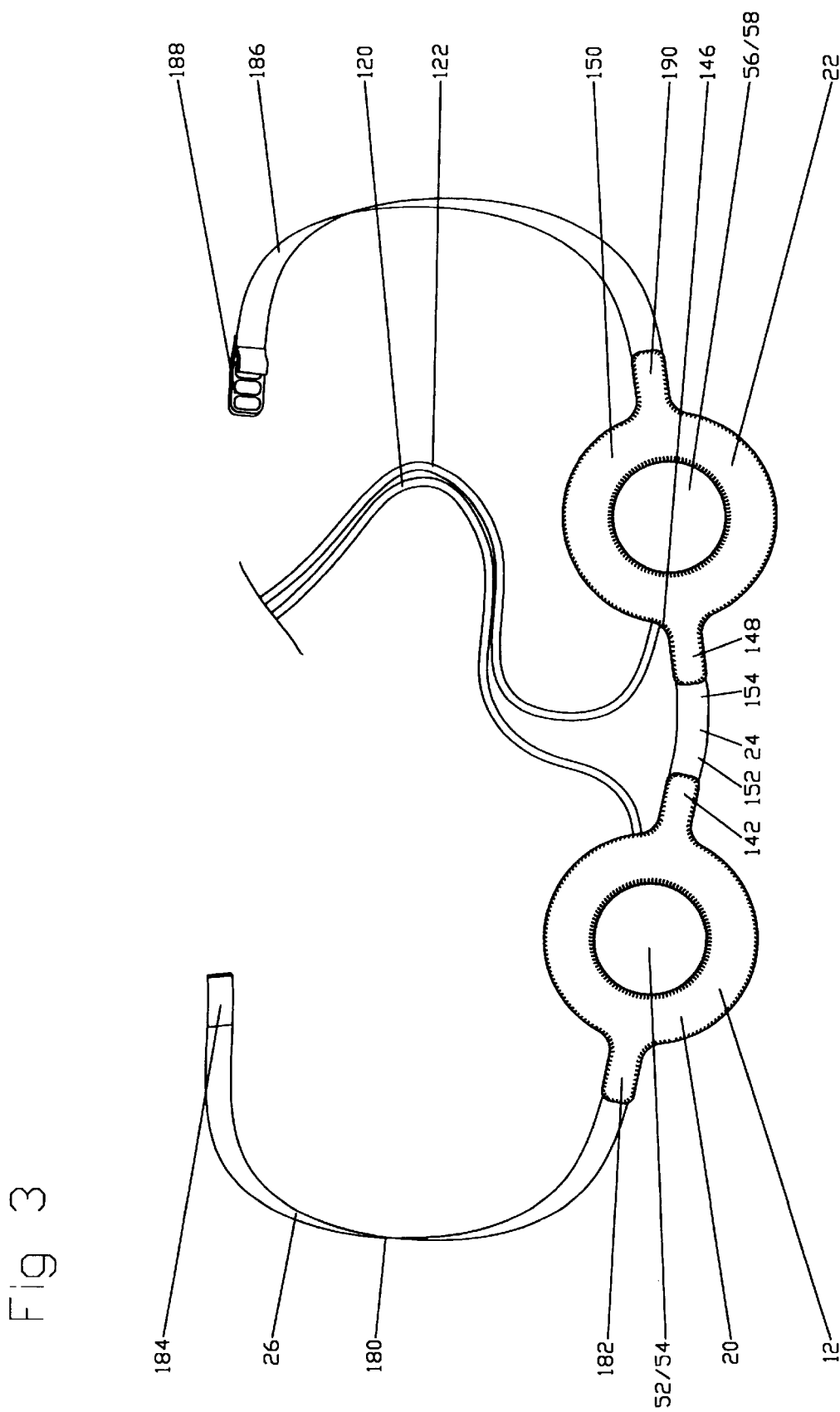
FIG. 3, is a diagrammatic, perspective, view of the outer surface of the harness of FIG. 2, with connecting cables foreshortened for clarity.

With general reference to FIGS. 1–10, there is provided a system 10, which allows breast surface temperatures to be measured, with great reliability, for periods of an hour or more at any desired rational sampling rate. Collected breast surface temperature data may then be downloaded into a computer, which forms part of the system, for elaboration using proprietary software which is also part of the system.
Preferred Embodiment In the preferred embodiment, system 10, comprises the principal elements of a mechanical adjustable harness 12, having a permanently connected remote monitor unit 14, an interface unit 16 and a host personal computer (PC) 18. Host PC 18, comprises a normal processor, VDU, mouse and keyboard (not illustrated).

It is important to note that mechanical adjustable harness 12, is not physically attached to the breast with adhesives or tape. Neither is harness 12, a brassiere, since it cannot provide support for the breasts and does not contain them, nor is it a brassiere insert since it is not necessary to use it in conjunction with a brassiere. Finally, harness 12, is not a garment, since it has no purpose or use as apparel and is used only in relation to its specific function, immediately hereinafter described.

System 10, is directed, by means of the function of its structural elements, towards the assessment and determination of the risk of developing cancer later in life, by the measurement of breast temperatures, over a period normally of one hour. Notwithstanding this, the instant invention may be used to detect breast cancer.

Harness 12, only one size of which is needed to fit all subjects, comprises two flexible, flat, ring-like contactor pads 20 and 22, united anteriorly by a short, adjustable, elasticated strap 24 and united posteriorly by a longer, adjustable and openable strap 26. Harness 12, may be used without a brassiere or in conjunction with the subject's own brassiere, if she indicates that she is discomforted without a supporting undergarment, according to the decision of the investigator. Each contactor pad 20, 22 comprises substantially similarly sized and shaped inner and outer layers 28; 30 and 32; 34, of flexible, compressible and extensible material preferably neoprene sheet 2.5 mm to 3.00 mm in thickness and provided with suitable flexible facing fabrics, such as the nylon material known commercially as Lycra™.

Each of contact pad layers 28–34, has two extension tabs 36–50, disposed about opposite ends of a diameter, for the attachment of anterior strap 24, and posterior strap 26. Contact pad layers 28; 30 and 32; 34, which are cut-out blanks, each have a central hole 52–58, preferably of 40 mm of diameter prior to assembly. During assembly, hereinafter described, this diameter increases to about 45 mm which is adequate to accommodate the areolar area of the majority of women. The outer diameter is preferably 100 mm before assembly and this decreases minimally upon assembly.

Contact pad layers 28–34, are laid one over the other, in pairs, for sewing, such that extension tabs 36–50, are aligned. By way of example, with particular reference to FIGS. 6 and 7, contact pad layers 28; 30, would be laid one over the other, aligned and then stitched together around the circumferences of central hole 52; 54. This is preferably accomplished with a zig-zag sewing machine set to a relatively large stitch and relatively low tension. The general appearance of the stitching is represented at 60. With some care and practice it will be found by those skilled in the art but not this novel technique, that the contactor pad layers, for example 28 and 30, may be pulled together in such a manner that the facings, two of which are indicated at 62 and 64, oppose at a join lying centrally between them, such that the neoprene itself is not exposed. This novel arrangement, together with other measures described hereinafter, imparts a pleasing 'bulked' feel to the construction of contactor pads 20 and 22.

Eight sensors 66–80, are arranged as two arrays 82 and 84, each of four sensors 66–72 and 74–80, respectively, on each of the inner contacting surfaces 86 and 88, of contactor pads 20 and 22, respectively. Sensor arrays 82 and 84, are disposed about inner contacting surfaces 86 and 88, in a regular manner, 90° apart along the circular center lines 90 and 92, lying between inner and outer boundaries 94; 96 and 98; 100, of 20 and 22, respectively. If, for reasons of explanation only, the upper portion of the vertical mid-line of each breast is regarded as North, the sensor positions are at North-East, South-East, South-West and North-West. By virtue of this arrangement, sensing means are provided to each of the well recognised anatomical quadrants of the breasts.

Sensors 66–80, are of the type AD592 supplied in a transistor can package of the generic type TO-92 and described in more detail, hereinafter.

Figure 5:
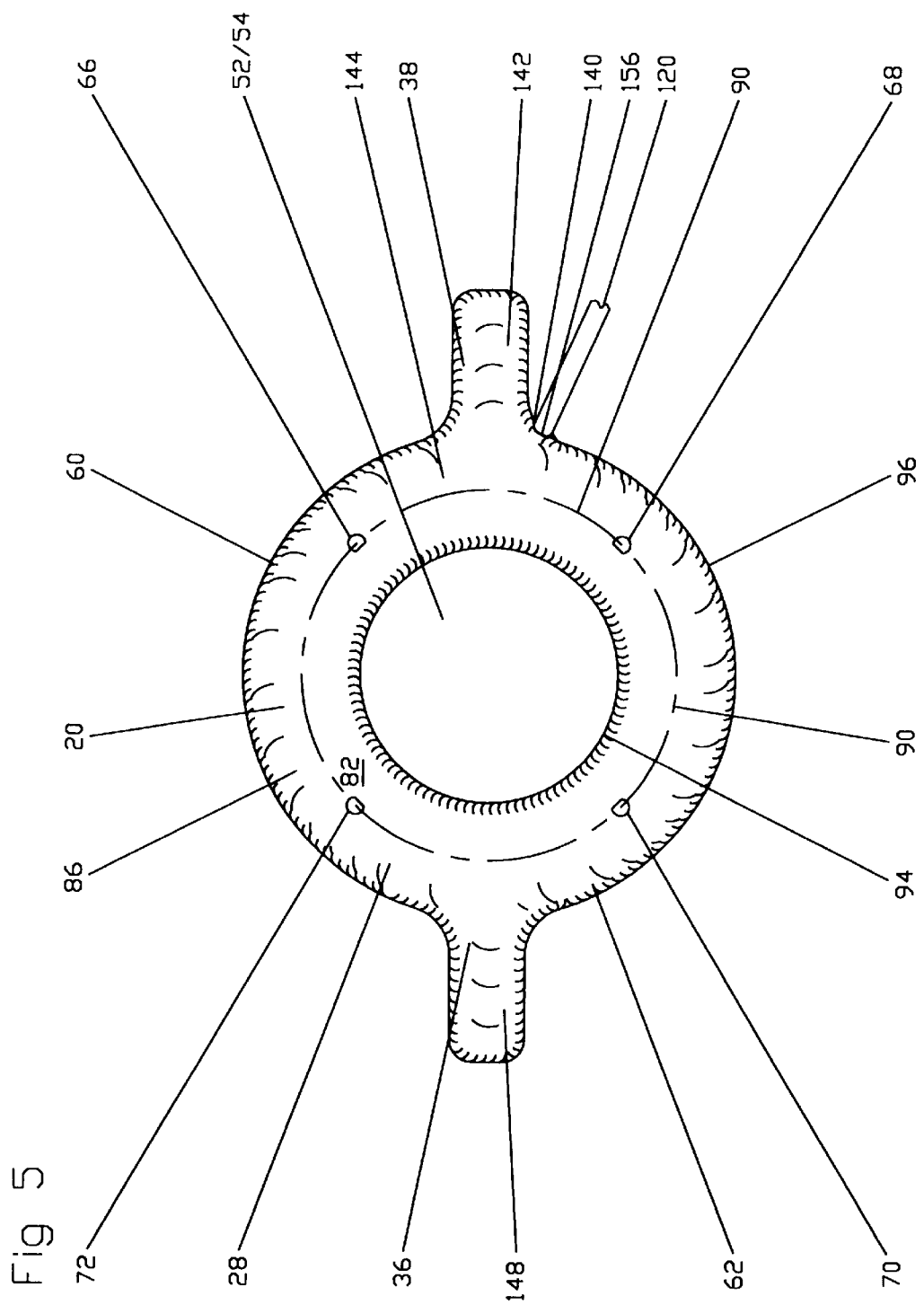
FIG. 5, is a plan view of the surface of one contactor pad assembly, according the present invention, showing a thermal sensor array.
Figure 6:
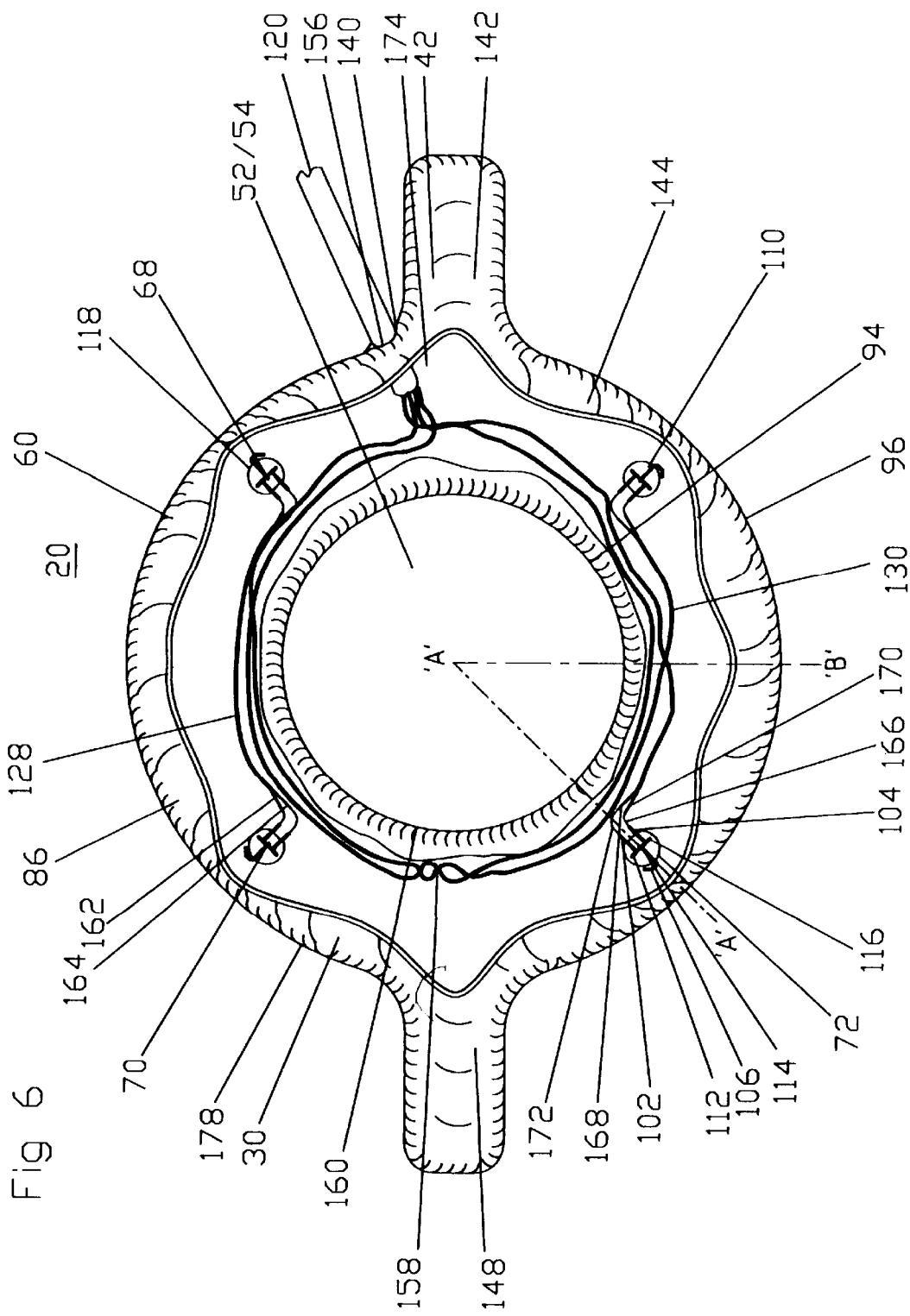
FIG. 6, is a cut-away plan view of one contactor pad assembly, from the outside or non-contact surface, showing sensor securing means and wiring arrangements.
Figure 6A:
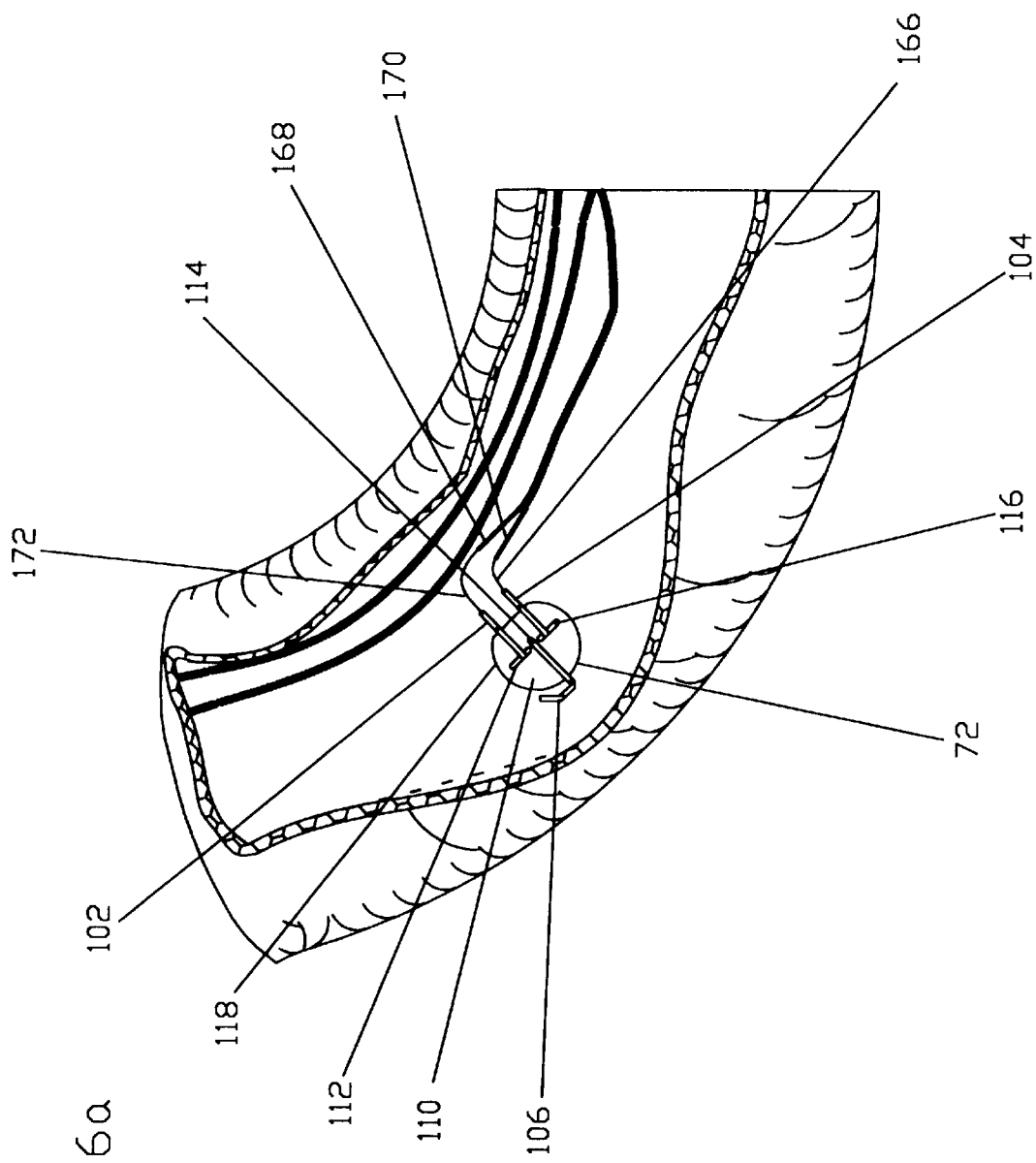
FIG. 6a, is an enlarged portion of FIG. 6, showing more clearly the wiring arrangements for sensor means.
Figure 7:
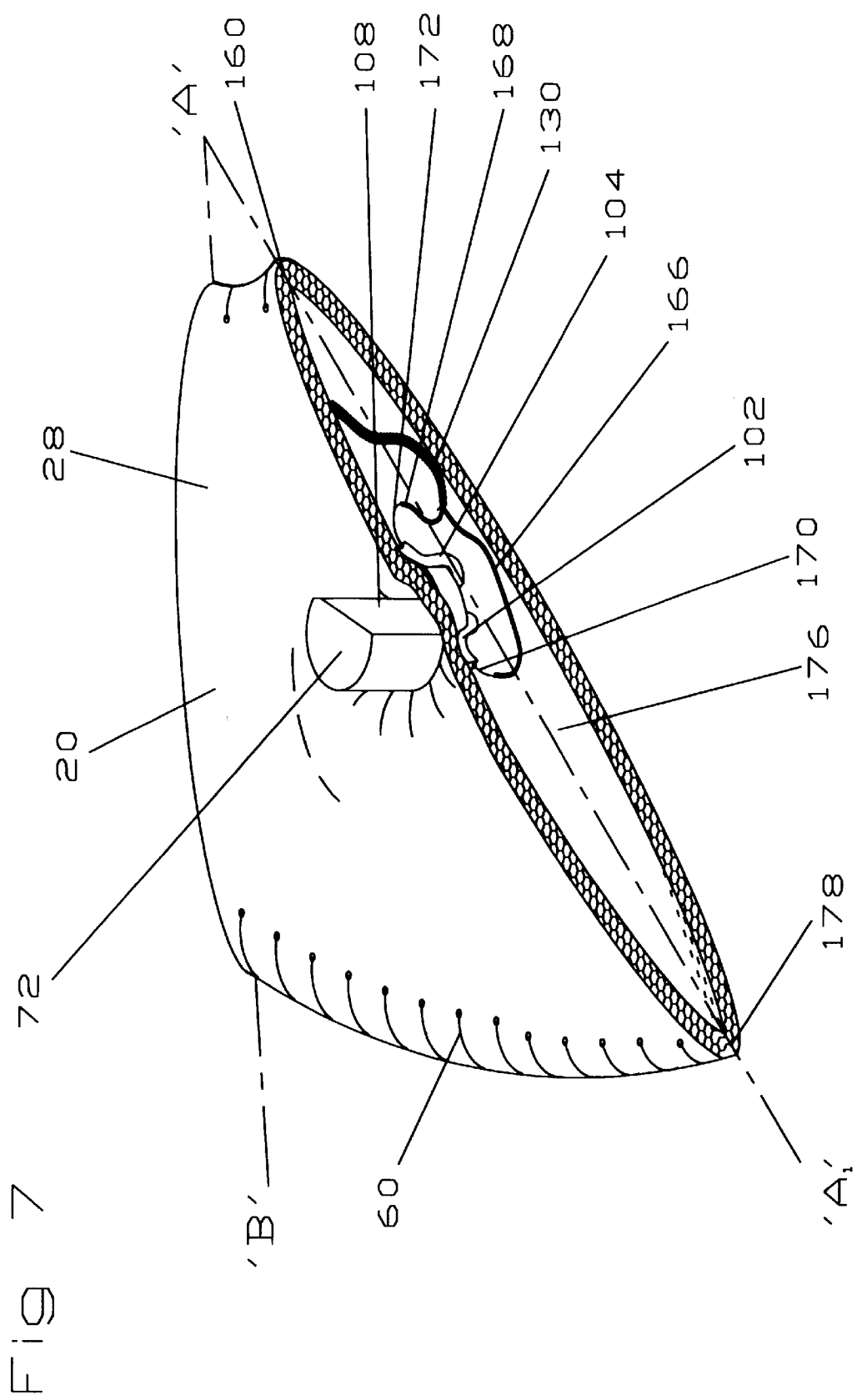
FIG. 7, is a partial, perspective, pseudo-section view of a segment of a contactor pad assembly, along line $A_1$-A and $A_1$-B showing construction details, a sensor and capture means therefor.
Figure 8:
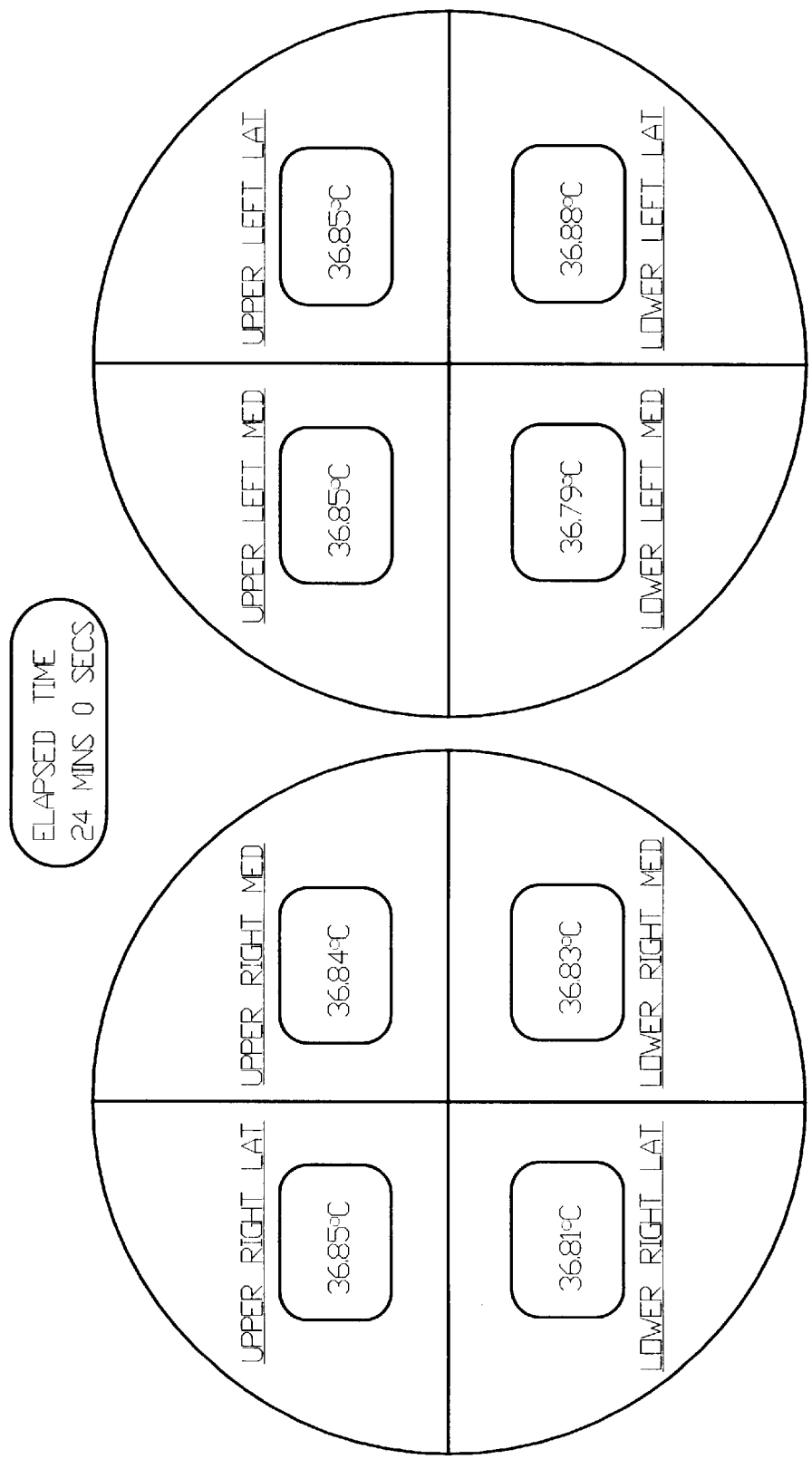
FIG. 8, is a diagrammatic view of a screen print, produced on a visual display unit (VDU) by a dedicated computer program, showing a pictorial and graphical representation of breast surface temperature data produced according to the present invention.

The method of deployment of sensors 66–80 and novel features of the associated wiring will be described with particular reference to FIGS. 5, 6 and 7, especially in respect of sensor 72. Each of sensors 66–80, has three stiff fine wire legs each about 1 mm wide, 0.5 mm thick and 10 mm long, closely disposed, 120° apart, those of sensor 72, being indicated at 102, 104 and 106. Each of legs 102, 104 and 106, is pushed carefully and firmly right through the material of inner contact pad layer 28. Advantage is taken of the small closed cell structure of the neoprene material which effectively renders the punctures of the material self-sealed by close compressive contact against each of legs 102, 104 and 106. All faces of type TO-92 sensor can package 108, are active and this is completely unsheathed, having no covering of any kind. This is in order to maximise contact with the breast surface and thermal transfer.

When correctly assembled to inner contact pad layer 28, legs 102, 104 and 106, of can package 108, protrude through the neoprene, and engage a small disc-like moulding 110, adapted by the provision of through holes 112, 114 and 116, disposed 120° apart near its periphery 118, to receive each of them, respectively. Disc moulding 110, is slightly larger than can package 108 and this causes legs 102, 104 and 106, advantageously to splay somewhat (not shown). By gently compressing disc moulding 110 and can package 108, together, against the neoprene of inner contact pad layer 28, the available length of legs 102, 104 and 106, protruding through holes 112, 114 and 116, in disc moulding 110, may be extended. Legs 102, 104 and 106, may then be bent over at periphery 118, of disc moulding 110, providing initial securing means for this assembly. As previously indicated, this method of introduction and assembly is applied to all of sensors 66–80 of both contactor pads 20, 22.

Cable connecting means between sensors 66–80, and monitor unit 14, are in the form of light, flexible plastics sheathed outer cables 120 and 122, each provided with four twisted pairs of inner cables 124–130 and 132–138, the number of pairs being the same as the number of sensors provided on each contactor pad. For reasons of clarity it has been necessary to exaggerate the size of inner cables 124–130 and 132–138, in FIGS. 6 and 7.

A different color outer is used for each of sheathed outer cables 120 and 122. This is to serve an important convention, during use, according to which the same first color is always used for the sheathing outer of the cable serving the left breast and similarly the same second color is always used for the sheathing outer of the cable serving the right breast. In the preferred embodiment I have used grey for the sheathing outer of the cable serving the left breast and violet for the sheathing outer of the cable serving the right breast, however, the important point is that the color difference must be obvious.

Sheathed outer cable 120, is secured, ultimately, in the angle 140, formed between extension tab 142 and the main body portion 144, of contactor pad 20, emerging along a generally medial path between layers 28 and 30. Similarly, sheathed outer cable 122 is secured, ultimately, in the angle 146, formed between extension tab 148 and the main body portion 150, of contactor pad 22, also emerging along a generally medial path between layers 32 and 34.

Extension tabs 142 and 148, provide anchor points for first and second ends 152 and 154, respectively, of adjustable, elasticated strap 24. First and second ends 152 and 154 of adjustable, elasticated strap 24, are secured in place by sewing.

Wiring details will be described with particular reference to FIGS. 6 and 7 and especially contactor pad 20. However, it is to be noted that wiring routing is accomplished according to a novel strategy directed towards ensuring that individual sensors are never subjected to traction in normal robust use. In particular, connections to those sensors which lie medially namely 66 and 68, in the case of contactor pad 20, are closest to the point of entry/emergence 156, of sheathed outer cable 120, in angle 140. Connections to sensors 66 and 68 are provided by twisted pairs 124 and 126, of sheathed outer cable 120, from which a sufficient length of sheathing is stripped away to allow them to be extended, in opposite directions, right around inner surface of inner sewn seam 160, disposed between contact pad layers 28; 30 and about central hole 52/54, before being routed back to sensors 66 and 68. At the point furthest away from point of entry/emergence 156, twisted pairs 124;126, are twice passed under and over one another, indicated at 158 and then drawn gently against the inner surface of seam 160, in such a manner that the tension applied does not cause distortion of central hole 52/54.

The restraint provided by routing twisted pairs 124 and 126, 'out and back' and by doubly overlapping them, before re-directing them to sensors 66 and 68, together with other measures shortly hereinafter described, provides such a high level of protection against traction on the sensors that it is not necessary to apply this strategy to remaining two twisted pairs 128 and 130, which are connected to sensors 70 and 72, which although furthest away from point 156, are shorter. The routing strategy may, however, be applied to twisted pairs 128 and 130, in full or in part, if so desired.

Sensor connection details will be described with particular reference to sensor 72. In FIG. 6, it may be seen that, by way of example, twisted pairs 128 and 130, each have a short section untwisted to provide single line connecting portions, indicated at 162;164 and 166;168, for sensors 70 and 72, respectively. As may be seen with brief reference to FIG. 7, very short bare wire ends, indicated at 170;172, are provided on each of 166;168, respectively. Bare wire ends, 170;172, are soldered to legs 102 and 104, respectively of sensor 72, leg 106 not being required in the circuitry employed.

Insulating means, which are also flexible cushioning means and adhesive means, are in the form of a hot melt insulating and sealing compound such as that supplied by Messrs Bosch AG, Germany, which is soft-setting and also translucent when initially cured. With contactor pad layer 30 gathered and held clear, the compound is introduced intimately about sensor legs 102–106 and soldered bare wire ends 170 and 172. This process is repeated for all sensor connections on both contactor pads 20 and 22. The process is extended by spreading a layer, several millimeters thick, over and about twisted pair connecting wires 124–130 and then, all over the interior of contactor pad layer 28. Particular attention is paid to the area about and around the inside of seam 160 about central hole 52/54. Contactor pad layer 30, is then released and the compound applied carefully in the area indicated at 174, in FIG. 6, where sheathed outer cable 120, upon sewing, comes to lie within the outer margins 96 and 100, of contactor pad layers 28; 30. The compound mass is indicated at 176, in FIG. 7. At a point when compound 176, has begun to cure but is still generally extrudable, contact pad layers 28; 30, are pressed together and then sewn around outer margins 96 and 100, to form outer seam 178, in a manner substantially similar to that hereinbefore described with reference to seam 160, of central hole 52/54. When constructed with the materials and assembled according to the method immediately hereinbefore described, contactor pads 20 and 22, are soft, flexible and formable and have a pleasing, compressible, 'bulked' feel.

Completed contactor pad assemblies 20 and 22, are 'handed' left and right by virtue of differently colored sheathed outer cables 120 and 122, each being directed medially. Contactor pad assemblies 20 and 22, are fitted with a short elasticated and adjustable anterior strap 24, by sewing respective first and second ends 152; 154, thereof, to medially directed tabs 142 and 148, respectively, on contactor pads 20 and 22. Medially directed tabs 142 and 148, are formed during the sewing together of 34; 38 and 42; 46, according to the procedure referred to in the preceding paragraph.

A first portion 180, of a longer elasticated, adjustable and openable posterior strap 26, is sewn to laterally directed extension tab 182, on contactor pad 20. Free end 184, of 180, is oversewn to prevent fraying. A second portion 186, of strap 26, is fitted with a slot-ring adjuster buckle 188. Second portion 186, is sewn to remaining laterally directed extension tab 190, on contactor pad 22, to complete the construction of harness 12.

Colored sheathed outer cables 120 and 122, are preferably about 900 mm in length and are of a softness such that they drape readily under their own weight. Cables 120 and 122, terminate within the case 192, of monitor unit 14.

With particular reference to FIGS. 9 and 10, monitor unit 14, has electronic micro-circuitry based around a PlC16C65 microprocessor. This is used to control the data collection, storage and subsequent downloading of the recorded data. Monitor unit 14, receives input from sensors 66–80, which are precision temperature monitor ICs, type AD592 (Analog Devices Inc., Mass., U.S.A.) having three fine wire connecting legs, only two of which are used in the electrical circuit. This type of IC is of the 'temperature in—current out' type and has excellent linearity and stability over the required operating range. Although up to sixteen AD592 sensors can be monitored and information from them recorded and stored in monitor unit 14, only eight are used in this preferred embodiment. Each of sensors 66–80, is polled in turn and this is achieved by multiplexing each of them in sequence, though this occurs with extreme rapidity. Analogue multiplexers, type AD506 (Analog Devices Inc., Mass., U.S.A.) are used to achieve this and the polling routine is run every sixty seconds and continued for one hour. Each of the sensors are individually calibrated using analogue multiplexers to switch in two calibration resistors for each individual sensor. The calibration resistance values are set by an independent calibration reference laboratory, prior to supply to any end user, to establish both zero and absolute current values against calibrated reference temperatures, to within 0.01° C. By these means, and in contradistinction to prior art devices intended for mass screening of breast surface temperatures, it is established that temperatures measured with the device are both accurate and absolute. The use of absolute calibration in the instant system is the underlying reason for the permanent connection between harness 12 and monitor 14, via cables 120 and 122. Each of the readings from sensors 66–80, are fed into an operational amplifier, which conditions the signal so that it may be processed. This is achieved by converting the analogue signal into a digital one using a 12-bit analogue-to-digital converter. Once in digital form, the data is stored in two 32K static RAM chips; the operation of writing and addressing being controlled by the microprocessor.

The time between readings and their duration is controlled by the microprocessor. After a set of readings has been taken, the readings are stored in the static RAM until the microprocessor is instructed to download data to host PC 18. The interaction between host PC 18 and monitor unit 14, is achieved by using a serial RS232 interface link. Commands are sent to the microprocessor of monitor 14, which controls the outflow of data to host PC 18.

System variables, such as duration of the testing cycle and time between readings, can be set from within host PC 18 and downloaded, via the RS232 link to monitor unit 14, where they are stored in a non-volatile EEPROM. Once in the EEPROM, these new values will be applied to the taking of readings. These are protected 'system engineer' functions and cannot ordinarily be accessed by persons using system 10, for measuring breast surface temperatures.

Power for monitor unit 14, is provided by a rechargeable PP3 9 volt Nickel hydride battery and voltage levels are controlled using regulator chips to set the correct voltage levels. Separate voltage levels are used for the analogue and digital parts of the circuit in order to reduce interference.

Monitor unit 14, is provided with a series of colored LEDs, best seen in FIG. 10. LED 194, is green and is lit briefly when the test cycle is started and every sixty seconds, thereafter, when sensors 66–80, are being polled for the purpose of taking readings. LED 196, is red and is lit steadily during the process of downloading data to host PC 18 and briefly during the process of re-setting, both hereinafter described. LED 198, is also red and is lit steadily in the event that monitor unit 14, is faulty and flashes regularly when a test cycle is completed. LED 200, is amber and is illuminated briefly when a manual re-set operation is carried out. LED 202, is green and is lit steadily when the battery of monitor unit 14, is being charged.

A temperature sensing cycle is initiated by depressing a plunger 204 and keeping it depressed for 2 seconds. Thereafter, depressing plunger 204, again has no effect. Although re-setting is normally carried out from within host PC 18, should there be a reason to abort a sensing cycle and start another, this may be accomplished by depressing a sub-flush manual re-set button 206, mounted in case 192, of monitor unit 14.

Upon completion of a testing cycle, monitor unit 14, is attached, via a connecting cable 208, which extends from socket 210, in case 192, to one of a series of substantially similar sockets exemplified by 212, on interface unit 16, as may be seen with reference to FIG. 1. Connecting cable 208, has substantially similar plugs 214 and 216, at both ends and is thus fully reversible. Interface unit 16, is permanently linked to host PC 18, by cable means. Interface unit 16, provides charging means for monitor unit 14 and this function is activated upon connection and continues whether monitor unit 14, is downloading or not.

Interface unit 16, provides plug-in charging and download services for a plurality of monitor units, typically up to twelve at one time, thereby facilitating the use of system 10, in high traffic clinic-based breast screening programmes.

Downloading of data stored within monitor unit 14, is accomplished by first selecting the channel to which socket 212, provides access. This is achieved by serially depressing a selector push-switch 218, until a reference LED 220, adjacent to socket 212, illuminates. As this is done it will be noticed that green LED 202, on monitor unit 14, illuminates and remains lit until 14, is disconnected from interface unit 16. Host PC 18, used for development, has a 100 MHz Pentium™ processor although most PCs having a 486, 100 MHz processor or better and capable of running the Windows 95™ operating system are adequate and the fact that most entry level machines are now much faster than this has no deleterious effect. Host PC 18, is provided with a dedicated programme written in Turbo-Pascal™ for Windows95™. This programme provides, under keyboard or mouse command, communication with monitor unit 14, via the RS232 link. Simple commands initiate data download, capture and saving of downloaded data, and display of the data in graphical and tabular numerical form for each of sensors 66–80. In addition the programme provides means for pictorial graphic display of the temperatures, measured by each of sensors 66–80, at each polling, displayed in their correct spatial positions on each breast.

Preferred Method of Use in Screening for Risk of Breast Cancer and Detection of the Disease The primary intended use for system 10, is in screening women between 20 and 50 years of age and who have not reached the menopause, to detect whether or not they may be at risk of developing breast cancer at some future date. System 10, is so designed that it may be readily used in large populations of women, within short time scales and involves the accurate measurement of breast surface temperatures.

Reliable epidemiological data exist on the incidence of breast cancer which suggest that as many as 1 in 12 women in Europe and perhaps 1 in 10 women in the U.S.A., dies from breast cancer and it is inevitable that in any large scale screening programme, numerous subjects will be tested who actually have the disease. Since it is also now known that breast surface temperature data, collected accurately at the appropriate point in the menstrual cycle, using progesterone assay to determine that point, are substantially similar in both the at-risk-but-with-no-disease-currently-present group and the active-disease group and further, that those data are different from the not-at-significant-risk group, the instant system 10, has potential for secondary use in confirmation of the presence of active disease.

In use, the subject to be investigated using the instant system, is counselled upon recruitment, as to the nature of the test. At least one month prior to the test, she is provided with a home-use urine dip test kit and a saliva collection kit. The urine dip test kit is in the form of a series of paper strips impregnated with a suitable agent which reacts to the surge of luteinising hormone in the urine which occurs at ovulation, by a color change from green to yellow. Such a test may be obtained commercially under the name Unipath™. The test is carried out by placing the strip into an early morning urine sample, collected shortly after waking each day, starting on the eighth day from the first day of bleeding of the last menses and continuing until the color change is observed upon testing. If the subject has a notional 28 day cycle, the color change will normally occur on day 15.

The saliva sample kit (not shown) is in the form of a series of 3 screw cap sterilised 5 ml saliva tubes and a strong, small, divided container suitable for transmission by post. On the day the color change is observed with the urine test, the subject collects a first saliva sample by dribbling a small amount into the first bottle which she then re-seals. The subject then collects a further two saliva samples on the morning of each of days 18 and 21. The samples should be kept in a domestic refrigerator until the series is complete.

If the color change in the urine dip test occurs earlier, probably indicating a shorter cycle, the first saliva collection is still made on the day the color change is observed, the second on the third morning thereafter (leaving two clear, non-collection days) and the third on the third morning after the second collection (also leaving two clear, non-collection days). Once the third and last saliva sample has been collected, the container containing all three samples is sealed and sent, by post, to a suitable laboratory equipped to carry out radio-immunoassay for progesterone levels. These results are used to measure and predict the most suitable date in the subject's next cycle to carry out the breast temperature test. One such commercial laboratory is BioClinical Services Ltd (BioClin International), Willowbrook Laboratories, St Mellons, Cardiff, Wales, UK.

Based on the results of the saliva progesterone assays from the laboratory, the investigator or investigating group select the appropriate day for the subject to attend a test center and invite her to do so. In a subject with a normal 28 day cycle this will normally be day 17 of the next cycle; in women with differing cycles it will normally be the 'day 17 equivalent'.

In a warm environment, where the ambient temperature should be maintained at 22° C.±2° C., the subject is provided with privacy and requested to doff her upper garments. With assistance from a female helper or nurse, the subject is fitted with harness 12, of the system 10. Harness 12, is secured in place with posterior adjustable strap 26. Anterior strap 24, is adjusted so that, when 24, is under tension, the pitch of central holes 50; 52 and 54; 56, in contactor pads 20 and 22, correspond with the pitch of the subject's nipples. Harness 12, is then adjusted on the breasts such that central holes 50; 52 and 54; 56, of contactor pads 20 and 22, are disposed concentrically about the nipples. The patient may, in addition, wear her own brassiere if she wishes, or a sports type elasticated brassiere or no brassiere. It is mandatory, however, that she wear a substantial and reasonably close-fitting over garment, such as a high-neck, medium-weight shirt, to limit or prevent any generalised heat loss. It is essential that identification details for both the subject and monitor unit 14, are recorded together and that the integrity of this combined information is maintained. It will be appreciated that only one size of the instant harness 12, is provided and required. The subject should be provided with a lightweight dressing gown having large pockets. I prefer to have these gowns modified so that there is a slit in the dressing gown material, parallel to and somewhat below the upper margin of the pocket and extending for most of its width. The edges of this slit should be oversewn with tape to prevent fraying and tearing.

Connecting cables 120 and 122, which extend between harness 12 and monitor unit 14, are led out from under the lower margin of the over garment and monitor unit 14 is passed through the slit in the dressing gown. Monitor unit 14, is supported until the test cycle is started. The subject is seated comfortably in the clinic setting and this should provide as welcoming and stress-free an environment as possible. It is helpful to provide her with reading materials.

The structure, design and sizing of contactor pads 20 and 22 and harness 12, in general, are such that not only is a good fit obtained on both large and small breasts with large and small areolar areas but excellent contact is also maintained between sensors 66–80 and both the superior and inferior aspects of the breast surfaces. Because contactor pads 20 and 22, are soft and conformable they readily mould to breast curvature, even on the concave upper aspect, unlike many prior art devices which, whatever their functional basis, are somewhat rigid and have a consequent tendency to 'tent' over the upper aspect, often holding functional surfaces away from the breast surface. It might be thought that the presence of small hard sensor cans 66–80, protruding from contactor pads against the breast surfaces would be uncomfortable or painful, however, contra-intuitively, tests under confidentiality arrangements on numerous subjects having breast sizes which varied from very small, through moderate, to very large, have all indicated that there is little awareness of the sensors at all and if any, it was usually only brief and immediately followed donning the harness. The term 'awareness' is chosen carefully since no subject reported pain or even discomfort. In all of these subjects, readings were obtained from all sensors throughout a one hour test cycle.

To start the test, the assistant, helper or other designated person, depresses plunger 204, on monitor unit 14, for 2 seconds, observing that green 'start' LED 194, illuminates briefly, to confirm initiation of the test. Once this has been done, monitor unit 14, is placed in a pocket of the dressing gown. Since plunger 204, is inactivated once the test has commenced accidental or deliberate interference with it has no effect. On the other hand, if there is a valid reason for interrupting the test, particularly if this involves removing or significantly readjusting harness 12, monitor unit 14, may be manually re-set by depressing sub-flush button 206, in case 192. The tip of a ball point pen is a convenient implement for accomplishing this and it will be noticed that amber LED 200, is lit briefly when this is done.

Throughout the test period, the subject should be encouraged to sit quietly and avoid exertion and should not imbibe hot or stimulating liquids. At the end of one hour the test will be complete and this may be confirmed by the person in charge of the test observing that red LED 198, is flashing regularly. The subject may then be taken back to the private cubicle to doff harness 12 and dress in her normal clothing, prior to departure from the test center.

At the end of a test cycle data from monitor unit 14, derived from the subject is downloaded into the host PC 18, as hereinbefore described during which process red LED 196 is lit steadily. As a general rule, data collected during the first forty-five minutes or so of the test should be discarded, since this period of time is necessary for the contactor pads 20 and 22, sensors 66–80, over garment and brassiere, if worn, to equilibrate and stabilise. Thereafter, a relatively stable pattern of temperature response from each of sensors 66–80, is a normal finding. These data are then evaluated by a skilled, trained person capable of comparing the subject's breast temperature data with known normal and abnormal data with a view to reaching a conclusion concerning whether or not the subject may be at risk of developing breast cancer at some future date.

In the event that the conclusion concerning the risk of developing breast cancer at some future date is positive, the subject would be informed promptly and invited back to participate first in a re-test and then in other tests. The purpose of these is to establish whether or not she may have existing cancer since, although the object of the test of the instant invention is not, primarily, to detect actual cancers, there will be some subjects who come forward who do have the undiagnosed condition. If she is negative to other tests for cancer, she will be informed that, according to the instant test, she may well be at a significant risk of subsequently developing breast cancer. This knowledge, far from being a prophecy of doom, allows surveillance, prevention and future intervention strategies to be planned and implemented with improved chances of preventing the disease or should it prevail later, successfully treating it, at an early stage. Handled well at counselling, it is eminently possible to engender a strongly positive psychological response in the subject. Alternatively, if the subject has already had other tests which suggest that she may have breast cancer or has physical signs which suggest breast cancer, the results from tests using the instant system may be used to confirm or deny previous findings.

On the other hand, if the test is negative, the subject will also be so informed. In this event, the subject may well be reassured, even to the point of euphoria and it is incumbent upon those who carry out the test to abjure such subjects that it is very much in their own interests to return for re-testing at a suitable interval, which may be, say, two years. In any case, a follow-up record and recall system must be maintained in order that all subjects tested can be called for a re-test after a suitable period, no matter how short or long this may be.

Experimental Observations

In a few subjects which I have encountered, the areolar areas have been exceptionally large and although this phenomenon has not been seen in very small breasts, it has been seen in some of relatively moderate size. Therefore, I have made and tested examples of harness 12, wherein the nominal external diameter of contactor pads 20 and 22, has been made 150 mm and the diameter of central holes 52;54 and 56; 58 has been made 80 mm. This variant is, in other respects, substantially similar to the preferred embodiment and has therefore not been further separately described.

The foregoing equipment of the instant invention is undergoing multiple phases of human trials at The European Institute of Oncology, Milan, Italy according to a protocol which reflects the general method of use immediately hereinbefore described, together with a rigorous statistical regime applied to the evaluation of the significance or otherwise, of data collected with this equipment and method. In addition, experiments have been conducted where the data collection method has been extended for several hours, in a statistically valid subset of subjects, to investigate whether intra-day temperature variations exist which would make a particular time of day most suitable for testing. Multiple experiments, conducted in accordance with the one hour testing regime and method hereinbefore described and with apparatus according to the present invention, have shown beyond doubt and in marked contradistinction to the Simpson and Green Chronobra™ device, that the instant invention does, indeed, collect breast surface temperature data in human females, from all sensors, to an accuracy of 0.01° C. In trials, it has been found that the system reaches equilibrium with the subject after about 45 minutes and temperatures then vary only over an extremely narrow range over the rest of testing period. Further multiple experiments, conducted off the human breast, have shown that the system monitors ambient temperature in the testing environment to the same degree of accuracy. Yet further experiments have detected abnormal breast surface temperatures in human females prior to but on the same day that they were diagnosed by other, standard, methods, such as biopsy and histology, as positive for breast cancer. Evaluation of these results is continuing.

From the foregoing, it will now be apparent that the present invention provides a system capable of making accurate measurements of temperatures on the surface of the human breast that is clearly differentiated from the prior art by its structure and which incorporates means to reliably record and store measurements of these temperatures and to manipulate and display them. Further, that use of the instant system, according to the method hereinbefore disclosed, constitutes a method for the assessment of the risk of future development of breast cancer in women who do not currently have the disease and for the detection of breast cancer in women who may have the disease.

It will be apparent to those skilled in the art that numerous modifications or changes may be made without departing from the spirit or the scope of either the present invention or its method of use. Thus the invention is only limited by the following claims.

I claim:

1. A device for measuring surface temperatures of human breasts, comprising:
    a harness including a first contactor pad, a second contactor pad, and a securing strap means associated with said first and second contactor pads to secure one of said contactor pads concentrically on each breast of the human subject, said first contactor pad including a first array of temperature sensors exposed on a breast contact surface thereof and said second contactor pad including a second array of temperature sensors exposed on a breast contact surface thereof to provide direct contact between each sensor of the sensor arrays and the surface of the associated breast;
    remote monitor means in communication with said first and second arrays of temperature sensors, to which a multiplicity of breast surface temperatures detected by the temperature sensors are communicated at predetermined intervals, and wherein such multiplicity of breast surface temperatures are stored as subject data.

2. The device of claim 1, wherein said remote monitor means is interfaced with a host computer, to which said subject data is transmitted and compared to known standard breast surface temperature data stored in said host computer.

3. The device of claim 2, wherein when said subject data is calculated by said host computer to be substantially similar to the said standard breast surface temperature data, an indication means of said host computer indicates the subject has a low long term risk of developing breast cancer; and when said subject data is calculated by the host computer to be higher by at least approximately 0.6° C. than said standard breast surface temperature data, said indication means indicates the subject has a substantially higher than normal long term risk of developing breast cancer.

4. The device of claim 3, wherein when said subject data is calculated by the host computer to be higher by at least approximately 1.2° C. than said standard breast surface temperature data, said indication means indicates the subject may have breast cancer.

5. The device of claim 1, wherein each of said contactor pads includes:

a soft, pliable inner layer having a central aperture, a front face defining said breast contact surface, and a plurality of holes therein to expose said sensors;

a soft, pliable outer layer having a central aperture concentric with said central aperture of the inner layer; and means for attachment to said securing strap means.

6. The device of claim 5, wherein each of said inner and outer layers includes a neoprene sheet, and said front face of said inner layer is a nylon sheet adhered to said neoprene sheet.

7. The device of claim 5, wherein said central apertures of the inner and outer layers are larger than about 45 mm in diameter, whereby average-sized areolar areas of the breasts of said subject are not covered by said harness.

8. A device for measuring surface temperatures of human breasts, comprising harness means provided with absolute temperature sensing means in the form of substantially similar first and second arrays each having a plurality of matched and calibrated sensor means and having connection means extending between each of said sensor means and a remote monitor means selectively connectable to an interface means, said interface means interfacing with a host computer, wherein:

said harness means is in the form of a harness comprising first and second contactor pads disposed apart so as to provide one for each breast of a human subject and anterior and posterior joining means which also constitute securing means for securing said harness to the human subject;

said first and second arrays of matched and calibrated sensor means each being disposed apart on a breast contact surface of each of said first and second contactor pads, respectively, and arranged such that no obstruction to thermal transfer is interposed between said sensor means and said human breast surfaces, said first and second contactor pads being so constructed as to prevent heat loss from all surfaces of said sensor means not in contact with said human breast surfaces and;

said connection means comprising first and second cables in contact with said first and second contactor pads and said remote monitor means, each of said first and second cables having an outer sheathing portion and an inner portion comprising a plurality of connecting wires, one of said connecting wires from said first cable extending from each of said sensor means forming said first array to said remote monitor means and one of said connecting wires from said second cable extending from each of said sensor means forming said second array to said remote monitor means.

9. The device of claim 8, wherein said remote monitor means comprises a housing provided with temperature monitoring cycle initiating means, power supply means, electronics means for selectively polling each of said sensor means of each of said first and second arrays at predetermined intervals in order collect output data therefrom, means for storing said data and means for downloading said data via said interface means to said host computer.

10. The device of claim 9, wherein said interface means comprises an interface between said remote monitor means and said host computer.

11. The device of claim 10, wherein said host computer comprises a computer and dedicated software program for the manipulation, elaboration and display of said data downloaded from said remote monitor means.

12. The device of claim 8, wherein said harness is provided in only one size to fit all subjects.

13. The device of claim 8, wherein said harness is adapted for use without a brassiere.

14. The device of claim 8, wherein said harness is operable when used with a brassiere.

15. The device of claim 8, wherein each of said first and second contactor pads is constructed from an inner annular layer and an outer annular layer substantially similar in size and shape to said inner annular layer, said inner and outer annular layers being formed as blanks from flexible, compressible and extensible sheet materials having a closed cell construction, said blanks each being adapted by the provision of an inner circular hole having a diameter selected so as to extend at least to the areolar area of the breasts of a majority of human females.

16. The first and second contactor pads of claim 15, wherein said inner and outer annular layers constituting each of said first and second contactor pads are joined together by overlaying one inner layer substantially upon one outer layer and sewing right around contiguous inner margins to form an inner sewn seam and contiguous outer margins to form an outer sewn seam.

17. The first and second contactor pads of claim 16, wherein each of said pads is provided with first and second extension tabs disposed at opposite ends of a diameter, said extension tabs constituting attachment means for said anterior and posterior joining and securing means.

18. The device of claim 17, wherein said anterior joining and securing means comprise adjustable strap means and said posterior joining and securing means comprise openable and adjustable securing strap means.

19. The device of claim 8, wherein each of said first and second arrays comprises an equal number of sensors.

20. The device of claim 19, wherein said sensors are of the 'temperature-in-current-out' type.

21. The sensors of claim 20, wherein said sensors are of the type AD592 supplied in a transistor can package of the generic type TO-92, said sensors having stiff wire legs.

22. The device of claim 21, wherein each of said legs of said sensors is pushed through said flexible compressible sheet material of said inner contact pad layers such that said material renders the punctures effected in said material self-sealed by close compressive contact of said material against each of said legs.

23. The device of claim 22, wherein each of said legs of said sensors protrudes through said flexible compressible sheet material and engages one of a series of through holes in a small disc-like moulding said holes being disposed 120° apart near the periphery of said moulding adapted by the provision of said holes to receive said legs.

24. The device of claim 23, wherein said plurality of connecting wires of said inner portions of said first and second cables are in the form of a plurality of twisted wire pairs and a first connecting wire of each twisted wire pair extends between a connecting point on a first of said legs of one of said sensors and said remote monitor means and a second connecting wire of each twisted wire pair extends between a connecting point on a second of said legs of the same said sensor and said remote monitor means, said twisted wire pairs of said first cable connecting means extending between said sensors of said first array and said remote monitor means and said twisted wire pairs of said second cable connecting means extending between said sensors of said second array and said remote monitor means.

25. The cable connecting means of claim 8 wherein said outer sheathing portions of said first and second cables are of different visually distinct colors.

26. The device of claim 15, wherein a wiring layout in respect of medially located sensor can packages mounted on each of said first and second contactor pads comprises extending first and second said twisted wire pairs provided by each of said first and second cables, in opposite directions, laterally and around inner surfaces of said inner seams of said inner circular holes of said first and second contactor pads such that at respective points substantially furthest away from points of entry and emergence of said first and second outer cables from each of said first and second contactor pads respectively, said first and second twisted pairs are passed under and over one another and drawn against said inner surface of said seam said first and second twisted pairs thence being routed back to said medially located sensor can packages, said wiring layout constituting anti-traction means for said sensor can packages.

27. The device of claim 8, further comprising insulating means, which also constitute flexible cushioning means and adhesive means, in the form of a soft insulating and sealing compound introduced intimately throughout the interior of said first and second contactor pads.

28. The device of claim 9, wherein said remote monitor means is provided with a plurality of channel means in the form of discrete electronic channels and channel connecting means for connecting said plurality of said sensors to said remote monitor means with said plurality of said twisted wire pairs, each one of said channels being adapted for connection to one of said sensors with one of said twisted pairs thereby providing means for the receiving of electronic signals from each one of said sensors into a discrete electronic channel.

29. The device of claim 28, wherein said remote monitor means is provided with means for individually calibrating each of said sensors using a plurality of analogue multiplexing means to switch in two calibration resistors for each of said individual sensors and resistance values of said calibration resistors are selected to establish both zero and absolute current values against calibrated reference temperatures.

30. The device of claim 28, wherein said signals from each of said sensors are analogue signals subsequently converted into digital signals which are then fed into an operational amplifier for conditioning such that said digital signals may be processed in a microprocessor.

31. The device of claim 28, wherein said digital signals are stored in a plurality of static RAM chips until said microprocessor is instructed to download data to said host computer.

32. The device of claim 28, wherein system variables may be set from within said host computer and downloaded via an RS232 link to said remote monitor means, where selected values of said system variables may be stored in a non-volatile EEPROM, from whence said selected values are applied to the collection of said signals.

33. The device of claim 9, wherein said power supply for said remote monitor means is provided by a battery.

34. The device of claim 30, wherein separate voltage levels are used for said analogue and said digital parts of the circuit and said voltage levels are controlled using regulator chips.

35. The device of claim 15 wherein said housing of the remote monitor means is provided with temperature monitoring cycle initiating means and a plurality of colored light emitting diodes to indicate function and status.

36. The device of claim 8, wherein said interface means provides plug-in charging and downloading means for a plurality of remote monitors.

37. The device of claim 11, wherein said display of said data derived from each of said sensors may include tabular numerical form and pictorial graphic display of the temperatures, measured by each of said sensors at each said polling, displayed in their correct spatial positions on each subject breast.

38. A method for measuring temperatures on the surface of human breasts of a subject, comprising the steps of:
    securing a harness to a human subject using a securing strap means such that a first contactor pad of said harness is disposed upon a first breast and a second contactor pad of said harness is disposed upon a second breast such that the nipple and areolar area of each of said first and second breasts are respectively located concentrically within an inner circular hole in each of said first and second contactor pads, with a plurality of sensor can packages of a first and second sensor array caused to lie directly upon the respective skin surfaces of each of said first and second breast, and said first and second contactor pads including absolute temperature sensing means having substantially similar first and second sensor arrays, respectively;
    activating a temperature monitoring cycle initiating means associated with a remote monitor means in communication with said first and second sensor arrays to initiate a temperature monitoring cycle for the collection of breast surface temperatures over a selected period during which each of a plurality of sensors of said first and second sensor arrays is polled at predetermined intervals and data so collected is stored within said remote monitor means;
    at the end of said selected period of said temperature monitoring cycle, said harness is doffed by said subject and said remote monitor means is connected to an interface means of a host computer by a cable connecting means; and
    downloading said stored data from said remote monitor means to said host computer under commands issued via a computer input device.

39. The method of claim 38, wherein prior to the step of securing the harness to the human subject, the day of ovulation is first determined and thereafter serial daily progesterone levels are measured to find day 17 of the menstrual cycle of the subject, and then waiting until day 17 of one menstrual cycle.

40. The method of claim 39, wherein said selected period for said temperature monitoring cycle is one hour.

41. The method of claim 40, wherein said predetermined intervals for polling each of said sensors are each sixty seconds.

42. The method of claim 41, wherein said serial daily progesterone levels are measured in saliva of the subject.

43. The method of claim 42, wherein determination of said day of ovulation is accomplished by serial urine dip testing carried out each morning following the last day of menses until a color change is noted indicating that ovulation has occurred.

44. The method of claim 43, wherein breast surface temperatures so determined during the first 45 minutes of any said temperature monitoring cycle are discarded to compensate for a period of equilibration of said harness to said human subject.

45. The method of claim 44, wherein breast surface temperature so determined after the first 45 minutes of any said temperature monitoring cycle are compared to known standard breast surface temperature data and;

where breast surface temperature so determined is substantially similar to said standard breast surface temperature data it may be reasonably concluded that the luteal cycle of the subject woman is present and this may indicate that there is a low long term risk of developing breast cancer;

where breast surface temperature so determined is higher by at least approximately 1° F. or 0.6° C. but by less than 2° F. or 1.2° C. than said standard breast surface temperature data it may be reasonably concluded that the luteal cycle of the subject woman is absent and this may indicate a substantially higher than normal long term risk of developing breast cancer and;

where breast surface temperature so determined is higher by approximately 2° F. or 1.20° C. than said standard breast surface temperature data it may be indicative of the presence of active breast cancer.

46. The method of claim 38, further comprising the step of recharging said remote monitor means in order that said remote monitor means may be prepared for subsequent use on another subject.

47. A device for measurement of temperatures on the surface of human breasts, comprising a system having harness means provided with temperature sensing means in the form of substantially similar first and second arrays, each of said arrays having a plurality of sensors and having connection means extending between each of said plurality of sensors and a remote monitor means selectively connectable to an interface means interfacing with a host computer means, said harness means being in the form of a harness comprising first and second annular contactor pads, said annular contactor pads being disposed apart from one another so as to provide a means for harnessing each breast of a human subject, and further comprising anterior and posterior joining means for securing said harness to said human subject;

said first and second annular contactor pads each being adapted by the provision of an inner circular hole having a diameter selected so as to extend at least to the areolar area of the breasts of a majority of human females when said breasts are respectively located concentrically within said inner circular holes in said first and second annular contactor pads;

said first and second arrays of sensors each being disposed apart on a breast contact surface of each of said first and second annular contactor pads respectively and arranged such that no barrier to thermal transfer is interposed between said sensor means and said human breast surfaces, said first and second annular contactor pads preventing heat loss from all surfaces of said sensor means not in contact with said human breast surfaces;

said connection means comprising first and second annular contactor pads and said remote monitor means each of said first and second cables having an outer sheathing portion and an inner portion comprising a plurality of connecting wires, each of said connecting wires from said first cable extending from each of said sensors forming said first array to said remote monitor means and each of said connecting wires from said second cable extending from each of said sensors forming said second array to said remote monitor means;

said remote monitor means comprising housing means in the form of a case provided with temperature monitoring cycle initiating means, power supply means to power an electronic means for electronically selectively polling each of said sensor means for each of said first and second arrays at rational intervals in order to collect output data therefrom, means for storing said data and downloading said data via said interface means to said host computer means;

said interface means comprising an interface between said remote monitor means and said host computer means; and said host computer means comprising a computer and dedicated software program for the manipulation, elaboration and display of said data downloaded from said remote monitor means.

48. The device of claim 47, wherein said harness is used without a brassiere.

49. The device of claim 47, wherein said harness is used with a brassiere.

50. The device of claim 47, wherein each of said first and second annular contactor pads is constructed from an inner annular layer and an outer annular layer substantially similar in size and shape to said inner annular layer, said inner and outer annular layers being formed from flexible, compressible and extensible materials.

51. The first and second annular contactor pads of claim 50, wherein said inner and outer annular layers constituting each of said first and second annular contactor pads are joined together by overlaying one inner layer substantially upon one outer layer and sewing right around contiguous inner margins to form an inner sewn seam and contiguous outer margins to form an outer sewn seam.

52. The device of claim 47, wherein said anterior joining and securing means comprise adjustable strap means and said posterior joining and securing means comprise openable and adjustable securing strap means.

53. The sensors of claim 47, wherein said sensors are of a temperature in—current out type.

54. The cable connecting means of claim 47, wherein said outer sheathing portions of said first and second cables are of different, visually distinct colors.

55. The device of claim 47, wherein a wiring layout in respect of first and second medially disposed sensors on each of said first and second contactor pads comprises laterally extending wiring means in the form of first and second twisted pairs of connecting wires provided by each of said first and second outer cables respectively above, below and around inner surfaces of said inner sewn seams of said inner circular holes of said first and second contactor pads such that at respective points substantially furthest away from points of entry and emergence of said first and second outer cables from each of said first and second contactor pads respectively, said first and second twisted pairs of connecting wires are passed under and over one another and drawn against said inner surfaces of said inner sewn seams, said first and second twisted pairs of connecting wires also being routed directly and medially to each of said first and second medially disposed said sensors, said wiring layout constituting anti-traction means for said sensors.

56. The remote monitor means of claim 47, wherein said remote monitor means is provided with means for individually calibrating each of said sensors using a plurality of analog multiplexing means to switch in two calibration resistors for each of said individual sensors and resistance values of said calibration resistors are selected to establish both zero and absolute current values against calibrated reference temperatures.

57. The device of claim 47, wherein said power supply for said remote monitor means is provided by a battery.

58. The device of claim 47, wherein said remote monitor means are provided with temperature monitoring cycle initiating means and a plurality of colored light emitting diodes to indicate function and status.

* * * * *